(12) United States Patent
Smith et al.

(10) Patent No.: US 8,467,583 B2
(45) Date of Patent: Jun. 18, 2013

(54) MEDICAL IMAGING METHOD AND SYSTEM

(75) Inventors: Yoav Smith, Jerusalem (IL); Rakefet Czerninski, Mevaseret Zion (IL)

(73) Assignee: Yissum Research Development Company of the Hebrew University of Jerusalem Ltd., Jerusalem (IL)

(*) Notice: Subject to any disclaimer, the term of this patent is extended or adjusted under 35 U.S.C. 154(b) by 1214 days.

(21) Appl. No.: 11/910,271

(22) PCT Filed: Apr. 4, 2006

(86) PCT No.: PCT/IL2006/000424
§ 371 (c)(1),
(2), (4) Date: Jun. 16, 2008

(87) PCT Pub. No.: WO2006/106509
PCT Pub. Date: Oct. 12, 2006

(65) Prior Publication Data
US 2008/0260218 A1    Oct. 23, 2008

Related U.S. Application Data

(60) Provisional application No. 60/667,788, filed on Apr. 4, 2005.

(51) Int. Cl.
*G06K 9/00* (2006.01)
*A61B 5/00* (2006.01)

(52) U.S. Cl.
USPC ........... 382/128; 382/165; 382/167; 600/306; 128/922

(58) Field of Classification Search
USPC .................. 600/306; 128/922; 382/128, 167, 382/165, 118, 14
See application file for complete search history.

(56) References Cited

U.S. PATENT DOCUMENTS 4,813,000 A * 3/1989 Wyman et al. ............... 382/165
5,309,256 A * 5/1994 Takada et al. ............... 358/504

(Continued)

FOREIGN PATENT DOCUMENTS

WO  PCT/IL1997/000187    12/1997
WO       WO97/47235    * 12/1997
WO  PCT/AU2000/001379    5/2001

OTHER PUBLICATIONS

Nischik et al., "Analysis of Skin Erythema Using True-Color Images", Dec. 1997, IEEE Transactions on medical imaging, vol. 16, No. 6, pp. 711-716.*

*Primary Examiner* — Aaron W Carter
(74) *Attorney, Agent, or Firm* — Edward Langer Adv. and Patent Attorney

(57) ABSTRACT

A computerized method and system for detection and quantification of changes in color on skin or internal tissue or organs within the human body. Digital images of the skin or tissue containing an area of interest are analyzed using the software of the invention, based on at least one channel of the LAB color system. The invention calculates the intensity and distribution of color present within the predetermined area of interest, and results in display of at least one color information attribute. The invention allows color calibration of the image to be performed in relation to a reference label having predetermined colors which surrounds the area of interest, prior to the analysis. The invention allows a threshold analysis to be performed, which graphically depicts the size and location of areas exhibiting significant change in color, which is a determinant factor in medical diagnosis.

22 Claims, 21 Drawing Sheets

U.S. PATENT DOCUMENTS

| | | | |
|---|---|---|---|
| 5,544,256 A * | 8/1996 | Brecher et al. | 382/149 |
| 5,852,675 A * | 12/1998 | Matsuo et al. | 382/167 |
| 6,075,879 A * | 6/2000 | Roehrig et al. | 382/132 |
| 6,256,062 B1 * | 7/2001 | Endo | 348/223.1 |
| 6,328,567 B1 * | 12/2001 | Morris et al. | 433/215 |
| 7,251,362 B2 * | 7/2007 | Osawa et al. | 382/167 |
| 7,522,767 B2 * | 4/2009 | Baker et al. | 382/167 |
| 7,676,080 B2 * | 3/2010 | Itagaki et al. | 382/162 |
| 7,856,118 B2 * | 12/2010 | Kalla et al. | 382/100 |
| 8,000,777 B2 * | 8/2011 | Jaeb et al. | 600/476 |
| 8,009,884 B2 * | 8/2011 | Chio | 382/128 |
| 2002/0176105 A1 * | 11/2002 | Kawai et al. | 358/1.9 |
| 2002/0186875 A1 * | 12/2002 | Burmer et al. | 382/133 |
| 2003/0007071 A1 * | 1/2003 | Goto | 348/61 |
| 2003/0007687 A1 * | 1/2003 | Nesterov et al. | 382/167 |
| 2004/0240716 A1 * | 12/2004 | de Josselin de Jong et al. | 382/128 |
| 2004/0267102 A1 * | 12/2004 | Skladnev et al. | 600/315 |
| 2005/0036668 A1 * | 2/2005 | McLennan et al. | 382/128 |
| 2005/0228264 A1 * | 10/2005 | Grichnik | 600/411 |
| 2006/0204124 A1 * | 9/2006 | Aihara | 382/274 |
| 2008/0158626 A1 * | 7/2008 | Bang et al. | 358/518 |
| 2008/0260218 A1 * | 10/2008 | Smith et al. | 382/128 |

* cited by examiner

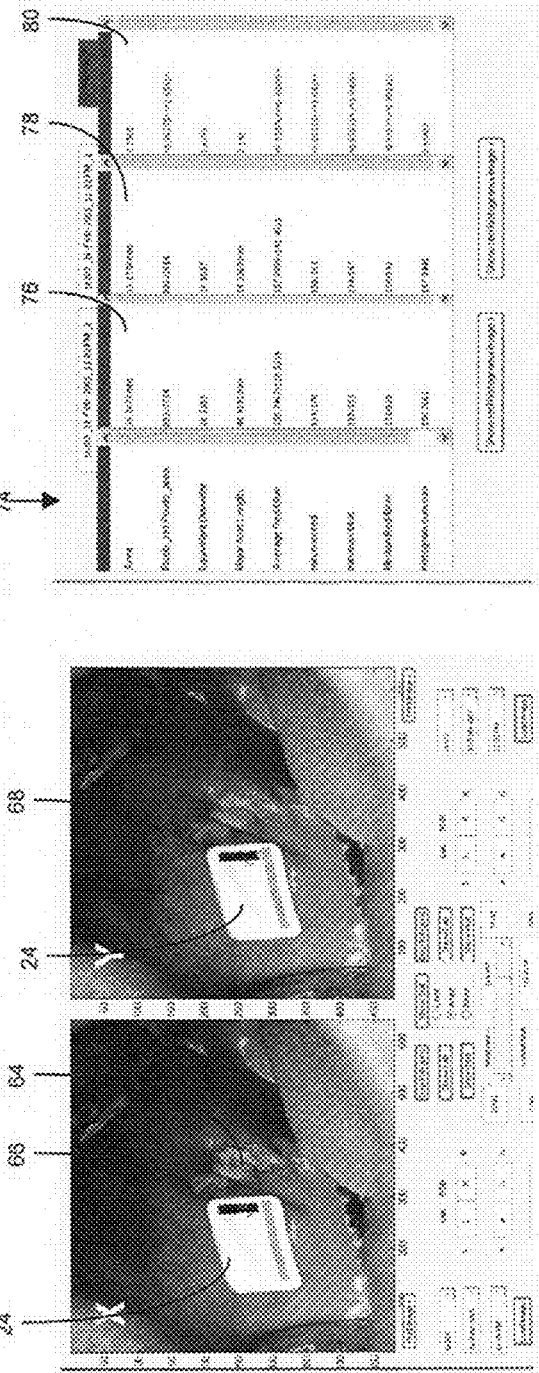
FIGURE 4
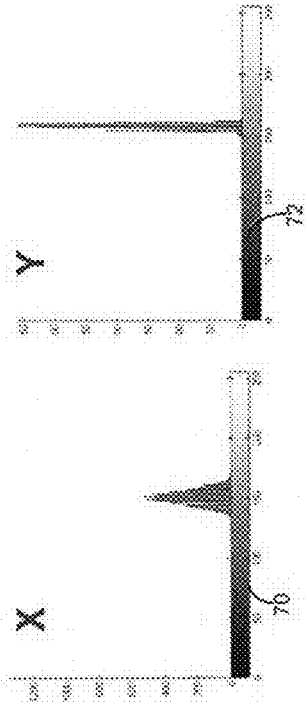

Development of lip carcinoma – follow-up after 2 months

Figure 16: calibrated image of palatal fungal infection
(candidiasis)
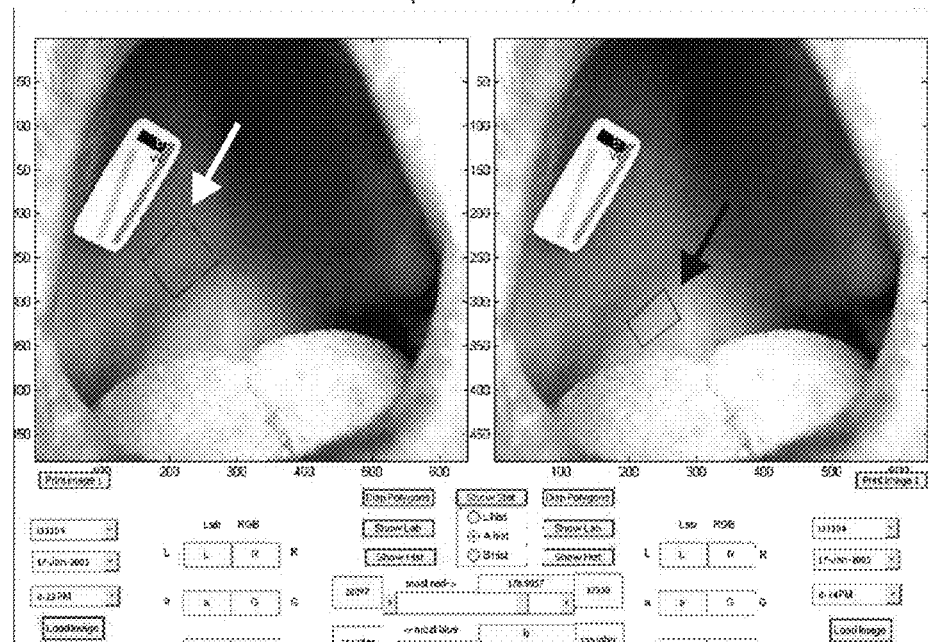
16A
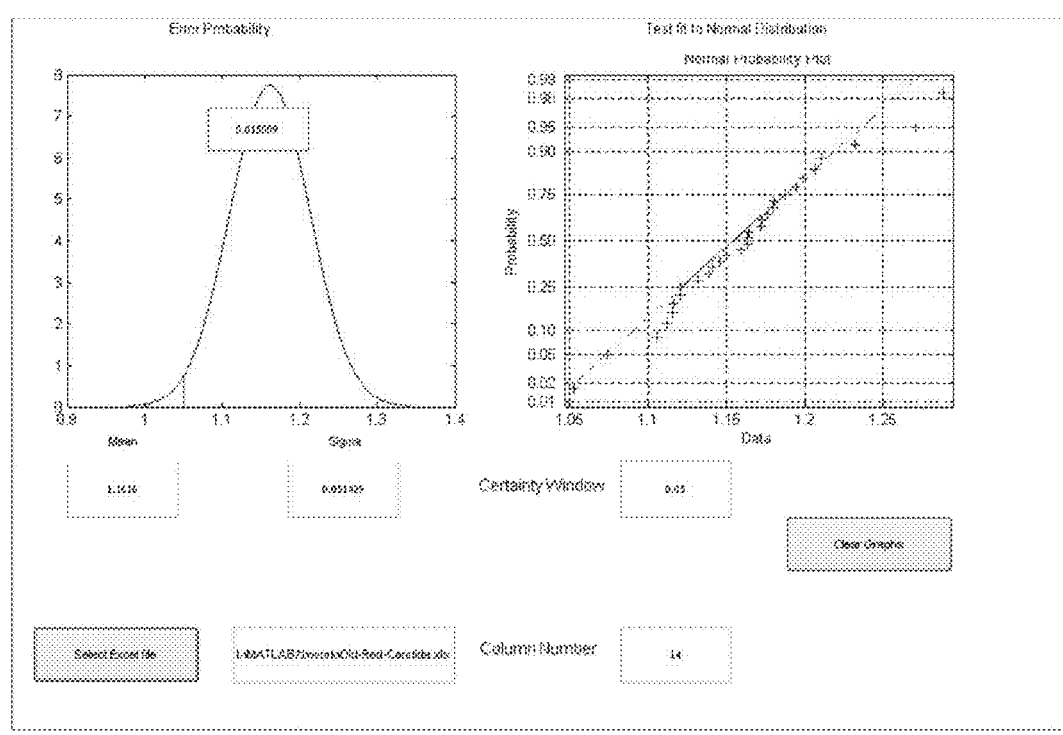
16B: Median red color ratio of normal versus fungal-infected tissue.

| | 111104_17-Jan-2005_8:24PM_2 | 111104_17-Jan-2005_8:24PM_2 | |
|---|---|---|---|
| Area | 49.5697 mm | 21.8134 mm | 2.2724 |
| Pixels_ref/Pixels_area | 423/5242 | 461/3514 | *0.91757*/*2.0851* |
| Equivalent Diameter | 21.6014 | 14.9595 | 1.444 |
| Major Axis Length | 24.4239 mm | 19.7914 mm | 1.2341 |
| Average Red/Blue | 185.8074/158.9781 | 153.3002/157.6087 | *1.2182*/*1.0084* |
| min/max red | 177/196 | 143/171 | *1.2463*/*1.1462* |
| min/max blue | 149/176 | 151/167 | *0.9867*/*1.0539* |
| Median Red/Blue | 186/158 | 152/157 | *1.2237*/*1.0064* |
| histogram cumsum | 185.8428 | 153.5613 | 1.2102 |

Figure 16C: color information attributes of normal versus candidia-infected areas Figure 17: Median red color ratio of normal versus inflamed tissue (Lichen Planus-erythomatous type)
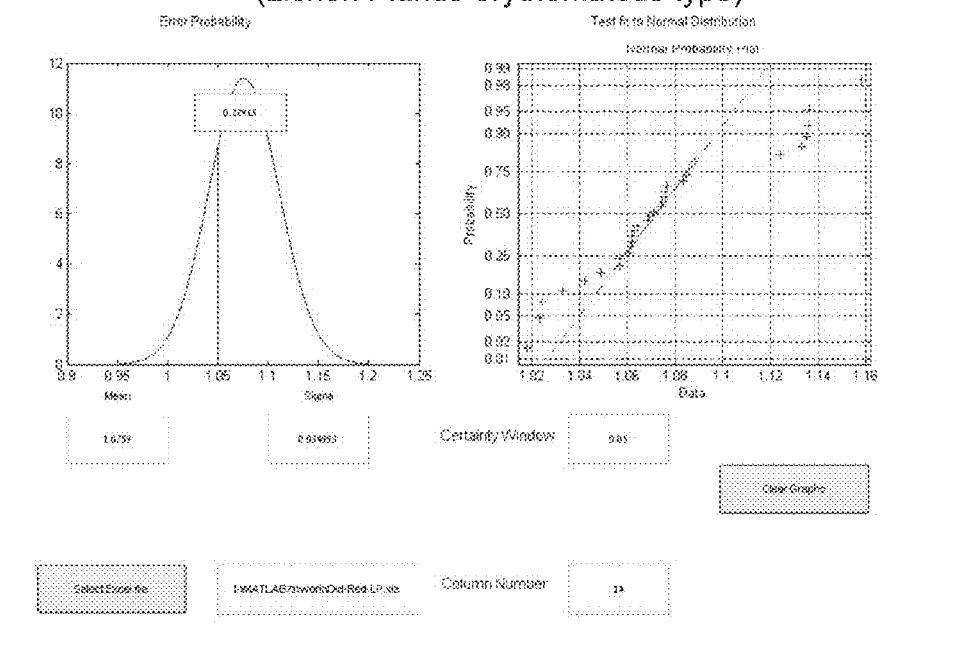
17A
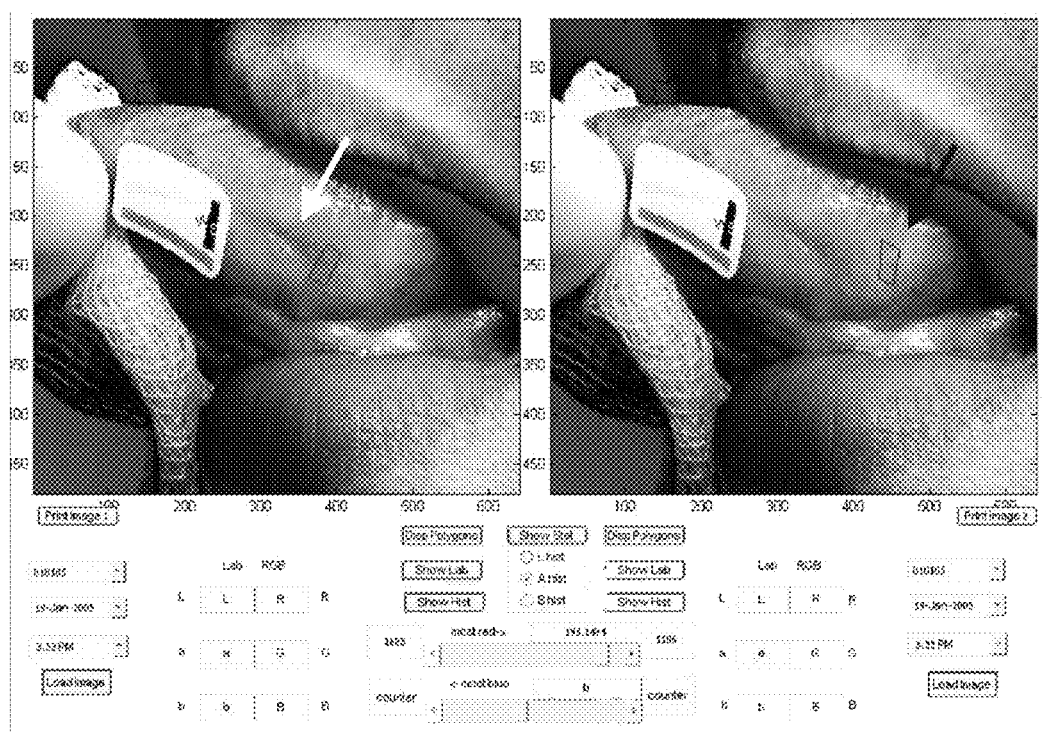
17B: Calibrated image of tongue with inflamed area

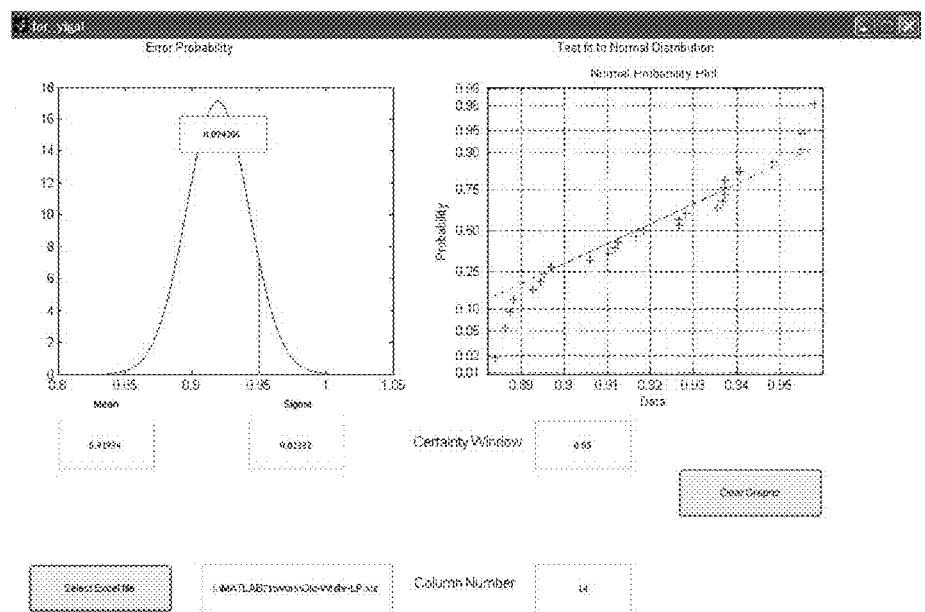
Figure 17C: Color information attributes of inflamed area
(Lichen Planus-erythomatous type)
Figure 18: Median red color ratio of normal versus inflamed tissue
(Lichen Planus-striated type)

Figure 19: Median red color ratio normal versus premalignant tissue (dysplasia) in buccal mucosa
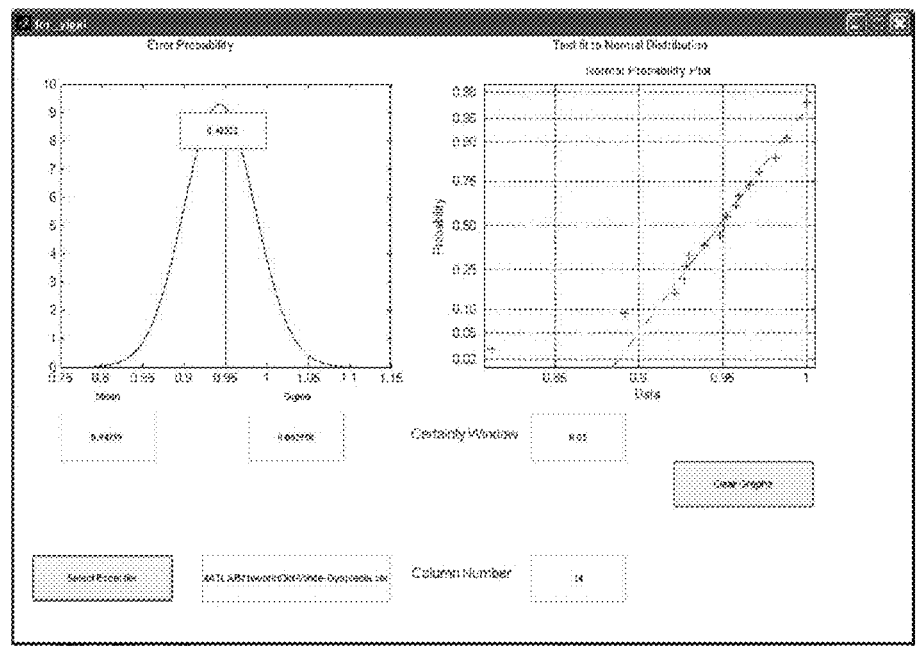
19A
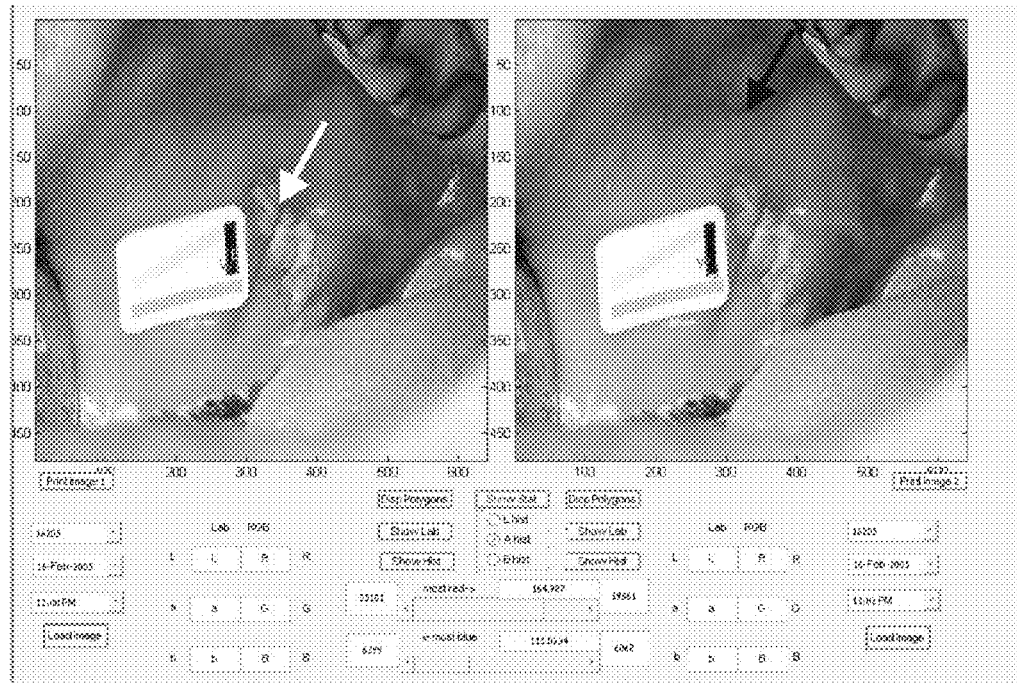
19B Figure 19C: Color information attributes, normal versus premalignant tissue (dysplasia)

| | 16205_16-Feb-2005_12:02 PM_2 | 16205_16-Feb-2005_12:02 PM_2 | |
|---|---|---|---|
| Area | 36.2673 mm | 13.1558 mm | 2.7568 |
| Pixels_ref/Pixels_area | 853/7734 | 886/2914 | «0.96275»/»2.6541» |
| Equivelent Diameter | 26.2383 | 16.1057 | 1.6291 |
| Major Axis Length | 41.4191 mm | 19.3369 mm | 2.142 |
| Average Red/Blue | 150.7467/128.5319 | 157.8899/141.4021 | «0.95476»/»0.90893» |
| min/max red | 134/170 | 150/163 | «0.89333»/»1.0429» |
| min/max blue | 115/153 | 134/147 | «0.85831»/»1.0408» |
| Median Red/Blue | 151/128 | 158/142 | «0.95577»/»0.90141» |
| histogram cumsum | 150.7662 | 157.9441 | 0.95455 |

[Show red histograma image 1] [Show red histograma image 2]

MEDICAL IMAGING METHOD AND SYSTEM

CROSS REFERENCE TO RELATED APPLICATION

The present application is based on International Application No. PCT/IL2006/000424 filed on Apr. 4, 2006, which is based on U.S. Provisional Application No. 60/667,788 filed on Apr. 4, 2005.

FIELD OF THE INVENTION

The invention relates to image analysis for medical purposes. More specifically, the invention relates to detection and analysis of changes in color on skin or internal tissue or organs within the human body.

BACKGROUND OF THE INVENTION

In current practice of dermal analysis and of oral and dental lesion analysis, the physician typically observes the suspected area with the naked eye, or more rarely with an episcope to illuminate the skin, and based on parameters of size, color and other aspects of the visual appearance, decides whether the lesion warrants further observation, medical tests or treatment. The examination and diagnosis are therefore highly subjective, and are dependent upon the medical practitioner's powers of observation and experience.

Occasionally the practitioner will recommend follow up observation in order to ascertain that no changes in size or coloration of the lesion have occurred. These changes suggest malignancy or other pathologies, such as inflammation. Typically the practitioner will record the general appearance, size (diameter) and color in his records. When the patient returns for the follow-up visit, reference will be made to these records, which are not always sufficiently detailed in order to allow proper comparison.

For instance, when the color is recorded, it is significant for diagnosis if changes have occurred in the intensity of the color, and the practitioner has no efficient means of recording or analyzing the color changes that occurred over time. Some medical practitioners have begun to record and retain an image of the lesion using a digital camera, in order to refer back to this image upon subsequent visits. The practitioner will usually try to photograph from a predetermined distance at each instance, so that the size of the lesion appears similar, as does the angle from which the image is recorded. Comparison is then performed by visual assessment of the recorded image, versus a more current image, or versus the physical lesion itself during examination.

However, the images are influenced by the ambient lighting present in the room, which changes during different times of the day and in different seasons. The images are similarly influenced by the specific camera and flash used. These affect the appearance of the digital image, and hinder comparison of the images, especially in regard to the color changes occurring.

Two early prior publications address this problem. WO97/47235, by the inventor, discloses use of a reference label containing reference colors, which is placed near the lesion, then photographed using any type of digital camera. The colors are then normalized according to this reference label, using computer processing, in order to eliminate the effect of changes in the ambient lighting. After normalization, the colors of the lesion can be compared to color-normalized images previously recorded.

U.S. Pat. No. 5,852,675 to Matsuo et al. similarly discloses various reference labels and algorithmic means of their computerized detection and analysis, which aim to eliminate the effect of changes in the ambient lighting, upon the color of digitized images. In addition to normalization of the colors, the labels disclosed in both U.S. Pat. No. 5,852,675 and in WO97/47235 allow normalization of the size and skew of the image.

A later publication, WO01/35827, discloses a handheld episcope for dermal lesion viewing, having a cone of reference colors to allow color normalization, and a video or digital camera inside the unit. Recording of the images is performed either by inclusion of a memory chip or by connection of the unit by cables to a computer. Normalizations are performed of the color, the size and skew of the image.

Even after normalization of the colors of digitized images, the comparisons performed in the prior art do not help determine how the colors have been affected over time. This is important for instance, in analysis and diagnosis of oral images, where lesions in which the color becomes more intensely red over time can signify malignancy, infection or inflammation. Reduction in the intensity of the redness can signify healing and a positive reaction to treatment. Changes in the color intensity of a dermal lesion that becomes more brown, or more intensely gray, can signify melanoma. Since the analysis of the degree of change is most often performed visually, it is highly subjective and inaccurate.

Even when the digitized image is analyzed using computer processing such as described in the aforementioned documents (WO97/47235 and U.S. Pat. No. 5,852,675), the processing and analysis focuses on determining whether changes in the size of the lesion occurred, such as border enlargement.

In WO97/47235, the analysis pertaining to changes in color allows the user to determine how many pre-selected points in the lesion underwent changes in color over time, however there is no means of quantifying the intensity of these color changes, and therefore there is no way to determine whether the changes are significant enough to warrant biopsy or further observation. Slight changes in color do not necessarily indicate activity in the lesion, and could be related for instance to tanning of the skin.

Additional measurements pertaining to color, which were disclosed in WO97/47235 relate to the average color of the entire lesion, which could be plotted as a histogram. Such a histogram does not help the physician establish whether the color intensity has changed to a significant degree at particular points within the lesion.

To date, there is no way in prior art to calculate and quantify whether a specific area of tissue or organ has become more intensely colored, signifying a suspected malignancy or inflammation.

Therefore, the need exists for an objective and quantitative method of analyzing the aspects of color present in a lesion. Such a tool would allow images to be compared and analyzed without being influenced by changes in the ambient light, and would grant the user a means of quantifying the color in the lesion, in order to determine the degree of change which has occurred in the lesion, and whether the changes are sufficiently significant to indicate malignancy or other undesirable biological changes are present. The method would allow evaluation of the degree of response to treatment, or of the degree of spontaneous healing of the lesion.

GLOSSARY

In the description of the present invention, the term "lesion" refers to an area of the human body having an abnormal appearance, such as swelling, unusual mass, coloration or ulceration and is not limited to premalignant or malignant lesions. The term includes moles and wounds.

In the present invention, the term "digital image" refers to a color image composed of individual pixels. The image is most preferably captured using a digital camera, but alternatively the image can be captured using a film-based camera, and can be converted using appropriate hardware and software into a digital image, for instance using a flatbed scanner, its accompanying software, and photo-enhancing software.

In the present invention, the term "color information attribute" refers to the results of mathematical calculations that give a quantified indication as to the color intensity and distribution within a given area of predetermined pixels.

SUMMARY OF THE INVENTION

It is an object of the present invention to provide a system and method for analysis of changes in color occurring in images of the human body. The invention can be used, among other uses, to assist in medical diagnosis of those diseases in which the intensity of the color is related to progression of the disease.

The present invention discloses a method and system, which allow the user to determine the extent and therefore the medical significance of color changes that are present in a tissue or organ of the human body. The invention allows quantification of the intensity of the colors, which is novel over prior art medical diagnostic technology.

The scope of the invention includes and allows evaluation of images from all body tissues and organs in which changes of coloration and size are relevant to the clinical diagnosis, to assessment of the effectiveness of treatment or to the progression or activity level of the disease.

In the prior art, such as in WO97/47235 to the inventor, the color system used was based on RGB color, with each digital point, or pixel, having a specific level of each of the three color components (red, green and blue). The amount of contrast (white versus black) is contained within this information, and is not separable from it. The naked eye erroneously perceives red images that are darker as being redder. These images have more black within them, but do not necessarily have more red within. The RGB color system does not allow expression or normalization of this problem. Images that are truly more intensely red, do not necessarily appear thus to the naked eye, and do not give appropriately high "R" values in the RGB system.

In contrast, the present invention is based on use of the LAB color system, also known as "CIELAB" or "L*a*b*" color systems (or color space systems). The LAB system separates the amount of light present in the image, from the determination of the color intensity. The "L" channel of LAB contains no color information, only information on the image itself, as it pertains to lightness and darkness. The "L" channel defines the level of black versus white in the pixel. The "A" channel defines the level of red versus the level of green in the pixel. The "B" channel defines the level of yellow versus blue in the pixel. The LAB system:

1) allows separation of the details and contrast level of the image from the coloration of the image.
2) In the LAB system, as opposed to the RGB system, all color and contrast relations are linear.

These two important aspects of LAB, allow its use in overcoming the aforementioned shortcomings of the RGB system, and allow true analysis of the intensity of the color, without being mislead by the information on the contrast level.

When an image is analyzed using LAB color, changes that occurred over time in the "A" channel represent quantification of changes in the true degree of redness.

In a preferred embodiment, the present invention provides a method for computerized analysis of color present in at least one image of the human body, comprising:
a) placing a reference label having a plurality of reference colors in the vicinity of a tissue or organ of the human body;
b) capturing a color image including the tissue or organ and the reference label, the image is a digital image or is converted into a digital image;
c) performing color calibration of the image using the LAB color system. The calibration comprises reading the color intensity value of at least one reference color from the reference label in the image, comparing said value to the true predetermined color intensity value of the reference color, and correcting the digital data of the image in at least one channel within the LAB color system, for color distortion;
d) selecting the borders of an area of interest within the image;
e) calculating the intensity and distribution of color within the area of interest using at least one channel of the LAB system, to give at least one color information attribute;
f) displaying the at least one color information attribute upon display means.

At least steps (c) and (e) are performed using processing means supported by dedicated hardware allowing color calibration and allowing calculation and display of said color information attributes.

In a preferred embodiment, the calculations performed in step (e) for determining said color information attributes are selected from at least one of the following: a cumsum value, a threshold analysis, a histogram of a single LAB channel, the average color value measured in a predetermined LAB channel, the median of a predetermined LAB channel, the minimum color value measured in a predetermined LAB color channel, or the maximum color value measured in a predetermined LAB color channel.

In a preferred embodiment, the present invention provides a system for analysis of color present in images of the human body, comprising:
a. a digital camera, or scanning means for converting image information into digital image information;
b. a reference label having a plurality of reference colors;
c. processing means comprising a memory device, a driver and display means, wherein the processing means is in communication with the memory device, and is configured to:
  i. perform color calibration of the image using the LAB color system, the calibration comprising reading the color intensity value of at least one reference color from the reference label in the image, comparing the value to the true predetermined color intensity value of the reference color, and correcting the digital data of the image in at least one channel within the LAB color system, for color distortion;
  ii. calculate the intensity and distribution of color within an area of interest using at least one channel of the LAB system, to give at least one color information attribute; and
  iii. display the at least one color information attribute upon said display means.

In a preferred embodiment, the color information attributes are selected from at least one of the following: a cumsum value, a threshold analysis, a histogram of a single LAB channel, the average color value measured in a predetermined LAB channel, the median of a predetermined LAB channel, the minimum color value measured in a predetermined LAB color channel, or the maximum color value measured in a predetermined LAB color channel.

The present invention further comprises a computer readable storage medium comprising software capable of:

a) performing color calibration of an image using the LAB color system, said calibration comprising reading the color intensity value of at least one reference color from a reference label present in an image, comparing said value to the true predetermined color intensity value of said reference color, and optionally correcting the digital data of the image in at least one channel within the LAB color system, for color distortion;

b) calculating the intensity and distribution of color within a predetermined area of interest using at least one channel of the LAB system, to give at least one color information attribute; and c) displaying said at least one color information attribute upon display means.

In a preferred embodiment of the computer readable medium, the calculations performed to give a color information attribute are selected from at least one of the following: a cumsum value, a threshold analysis, a histogram of a single LAB channel, the average color value measured in a predetermined LAB channel, the median of a predetermined LAB channel, the minimum color value measured in a predetermined LAB color channel, or the maximum color value measured in a predetermined LAB color channel.

It is to be noted, that though mention is made throughout, of malignancy and infection, the system and method of the invention are in no way limited to these uses. These are simply common uses. The scope of the invention encompasses all medical clinical uses in which color determination is an issue. These include for instance, follow up of burns, psoriasis, injuries, inflammation and microorganism related infection.

Also included are diagnoses and evaluation of malignant and premalignant lesions (e.g. erythroplakia, leukoplakia, carcinoma, leukemia), of pigmented lesions (melanin, vascular or iatrogenic in origin), inflammation resulting from local infections (such as abscesses or gingivitis) or from diffused infections (such as cellulitis). Bacterial infections (e.g. dental abscess), viral infections (e.g. herpetic infections), fungal infections (e.g. candidiasis, mucomycosis) or other infective organisms (e.g. leishmaniasis) can be detected.

Also included in the scope of the invention is analysis of reactive lesions that result from common irritants (e.g. smoking, local friction), immunologic disorders such as auto immune diseases and allergic reactions (e.g. contact stomatitis) and dermatoses (e.g. lichen Planus, Pemphigus) and granulomatous diseases (e.g. Melkersson-Rosental syndrome).

Changes in size can be followed using the present invention, in addition to the changes in coloration, and these changes in size are important in evaluating ulcerations such as apotheosis, vesiculoulcerative lesions, carcinoma or malignant lesions, infections, burns, as well as non ulcerative lesions such as pigmented lesions or white lesions.

Though dermal and oral lesions are primarily discussed in the Detailed Description, the scope of the invention is not limited to analysis of lesions, or to diagnostics upon the skin or within the mouth or teeth. The scope encompasses all types of medical analysis pertaining to color. The analysis may also include analysis pertaining to size and shape.

There is no intention to limit the invention to non-invasive uses, and use of the system and method of the invention can be envisioned, for instance, for rapid analysis of color changes of internal organs during surgery. This may ease a decision whether to perform more extensive or more invasive surgery.

One can envision, for instance, laparoscopic surgery during which images are recorded, preferably on digital media, then rapidly analyzed using the invention in order to determine whether significant color changes have occurred which warrant extensive surgery. Endoscopic, colonoscopic, or gynecological images, which are recorded, preferably on digital media, can be analyzed using the invention. Similarly, images originating from any part of the human body can be analyzed using the invention.

The invention is not limited to analysis of images recorded using digital media. Photos recoded using film negatives can be scanned using a common flatbed scanner, and saved as digital information in a computer memory, then analyzed using the invention. Other types of images originating from the human body, and recorded using unlimited technologies, can likewise be normalized and analyzed to determine the extent of color changes that have occurred, as long as the image captured, contains the reference label and as long as true color of the tissues or organs within the image is retained.

Other features and advantages of the invention will become apparent from the following drawings and description.

BRIEF DESCRIPTION OF THE DRAWINGS

For a better understanding of the invention with regard to the preferred embodiments, the present invention is herein described, by way of example only, with reference to the accompanying drawings, wherein:

FIG. 4 depicts two identical digital images of a white premalignant lesion in the oral cavity, and the color information attribute results of analysis of the image;

FIG. 16A illustrates images of palatal fungal candida infection versus normal tissue;

FIG. 16B shows statistical analysis of the results;

FIG. 16C depicts color information attributes of the tissue;

FIG. 17A illustrates statistical analysis of tissue inflamed due to Lichen Planus;

FIG. 17B depicts images of the tissue;

FIG. 17C depicts color information attributes of the tissue;

FIG. 18 illustrates statistical analysis of tissue inflamed due to Lichen Planus (striated);

FIG. 19A illustrates statistical analysis of pre-malignant buccal mucosa tissue;

FIG. 19B depicts images of the tissue; and

FIG. 19C depicts color information attributes of the tissue.

DETAILED DESCRIPTION OF THE PREFERRED EMBODIMENTS

It is appreciated that the detailed description that follows is intended only to illustrate certain preferred embodiments of the present invention. It is in no way intended to limit the scope of the invention, as set out in the claims.

The method and system of the present invention allow quantification of the color intensity and color distribution in a tissue or organ of the human body, after the image is captured as a digital image, or transformed into a digital image. The image is captured after placement of a reference label having several reference colors, adjacent to the tissue or organ.

Figure 1:
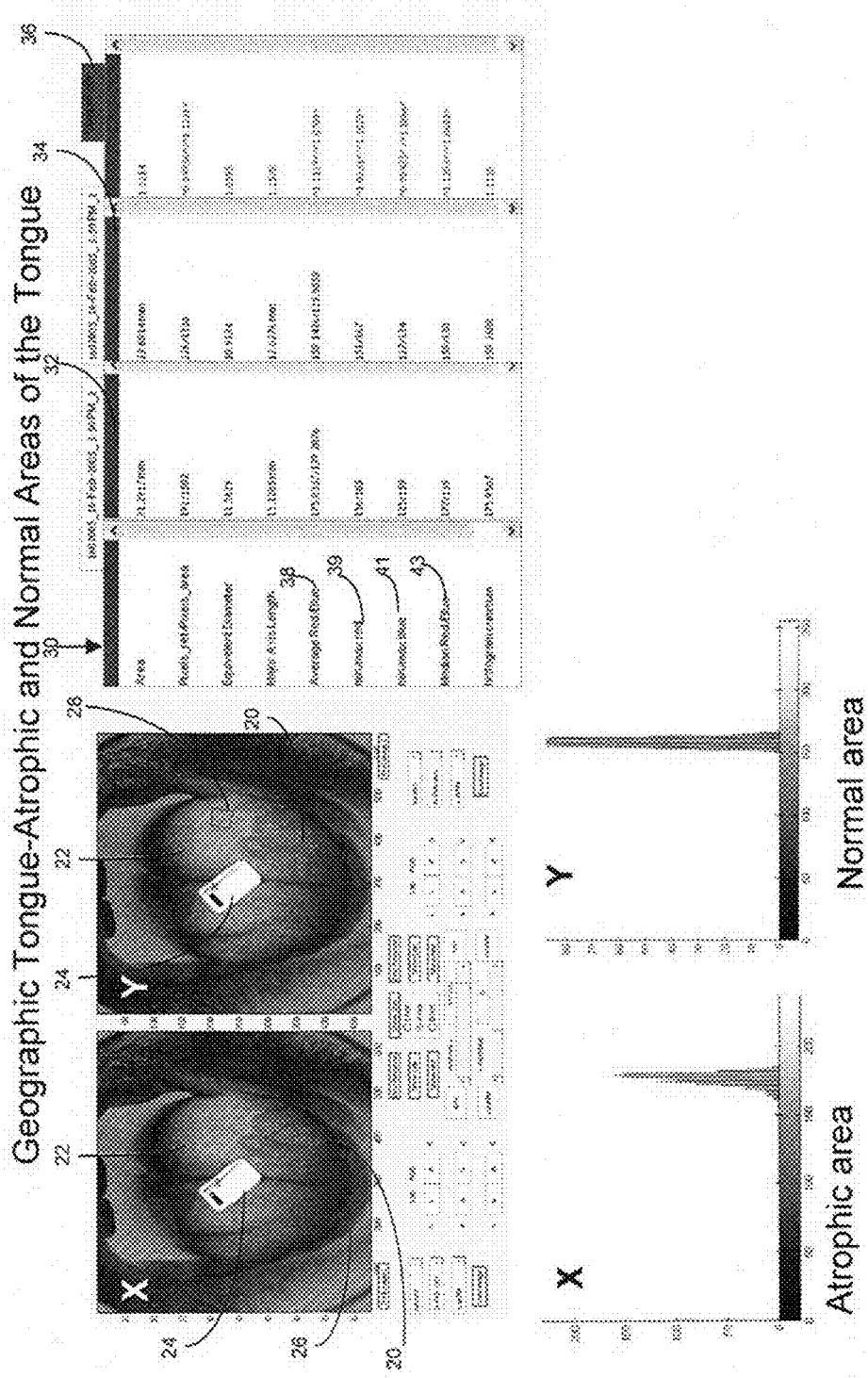
FIG. 1 depicts two identical digital images of a tongue having atrophic regions on it, and the color information attribute results after image analysis was performed on the image.

Typical use of the invention will now be described, on a patient having, for instance, an oral lesion. Referring to FIG. 1, there are presented images of a patient with atrophic regions on the tongue. Image analysis needs to be performed in order to determine the extent of the color changes that have occurred in the tongue. A reference label 24 having several reference colors (in this case, black, two shades of gray, and white) was placed on the center of the tongue 22 and the tongue 22 was then photographed using a digital camera. The image was transferred to a computer uploaded with the software of the invention.

Image correction was performed, by comparing the LAB color values of at least two reference colors of the reference label 24, as they appear in the image, with their true predetermined LAB values. If a discrepancy exists between the value of the reference color appearing in the image, and the true value of the reference color, the value of the discrepancy is displayed on screen, and the color of the entire image is then corrected based on the value of the discrepancy. This corrects for the lighting effects present in the room during capture of the image, and for variations in the color which result from use of various cameras.

An example of a discrepancy, is for instance, if the reference color measures in the image as having L=10, representing a certain shade of black in the L channel, when the true value of the reference color is in essence L=0 (blackest possible). A discrepancy of 10 exists, and the entire image is then corrected by shifting it 10 degrees to make it blacker. Correction is performed in each of the LAB channels. The corrected image is displayed on screen.

In order to compare the color intensity of the atrophied area 20 of the tongue 22 with that found in a normal area on the tongue, the area of interest is selected. In the image appearing at top left (referenced X), the borders of an area of interest (AOI herein) within the atrophied area were selected by the user, and drawn on the screen (shown as a faint trapezoid 26 on the bottom right of the image). In the image at right (referenced Y), the borders of an area of interest comprising normal tongue tissue were selected (faint square 28).

The intensity and distribution of color within each area of interest is calculated using the LAB system, and displayed, to give at least one color information attribute. These are mathematical indications as to the quantity of color present in the area of interest, and are based on the intensity measured in each individual pixel within the area. Each color information attribute can be displayed and compared with a similarly calculated attribute from a previously captured image of the same tissue, to determine whether improvement is seen in the medical condition over time.

Thus, the intensity and distribution of color can be quantified and followed over several weeks or months, in order to determine whether the extent of change is significant, indicating improvement or worsening of the medical condition. Alternatively, the color information attributes of two areas of interest originating from the same image can be compared, with one AOI representing healthy tissue, and another AOI representing diseased tissue. This will indicate the extent of the coloration change, at the present time.

The color information attributes are as follows:

A cumsum value (also termed a histogram cumsum) is a weighted average of the color intensity in the area of interest, answering the question "what is the most predominant color of the AOI?". In general, the calculation performed acts to group together pixels having similar color values, and calculates their portion relative to the number of pixels in the entire area of interest: A single LAB channel is selected, for instance in the atrophied tongue shown in FIG. 1, a change has occurred in the redness, therefore the A channel is of interest. The number of pixels within the area of interest (herein AOI) having a specific A (redness) value is multiplied by the numerical value of A at that specific value.

Then a second A (redness) value is multiplied by the number of pixels within the area of interest having the second A value, and these sums are added. If a third redness value is present in the AOI, this redness value is multiplied by the number of pixels in which it is contained. The results of these multiplications are summed, and then the result is divided by the number of pixels present within the AOI. Such a calculation can be performed in any LAB channel of interest. The formula for one such calculation is as follows (for instance, for a color value of 100, in the L channel):

$$\sum_{i=L}^{100} \frac{Pi * i}{N}$$

Wherein Pi is the number of pixels having a color value of i, and N is the total number of pixels in the image.

An example of measured color values and the cumsum calculation performed is as follows:

| i | Pi |
|---|---|
| 100 | 1000 |
| 50 | 500 |
| 20 | 200 |

$$\Sigma \frac{20*200 + 50*500 + 100*1000}{1700} = \text{CUMSUM}$$

A threshold analysis allows the user to select a threshold value of color intensity that is considered significant, and to display within the image, those pixels on the screen that are above or equal to that value.

For instance, pixels above a redness level of A=35 can be highlighted in fluorescent green on screen, superimposed upon the image so that the structures of the organs are still shown. This allows the user to see which areas of tissue are the most intensely colored, which may indicate for instance, the best area within the lesion, to select for a biopsy, since this area has the highest biological activity. Surprisingly, these are often different areas within the lesion, than those that would have been selected using only visual inspection.

The threshold analysis, which best identifies the color distribution within the image, can give a visual indication as to the severity of the disease, since it graphically depicts the size and location of areas having significant change in color. This allows the medical practitioner to decide whether further treatment is necessary. A practitioner can use the threshold analysis calculation in order to answer, for instance, the question "is the AOI 15% redder than the last visit?". This allows the practitioner to quantitatively measure changes occurring in the image over time.

A histogram of a single LAB channel can be shown, to indicate how many pixels in the image have each color value. Referring for instance, to FIG. 1, the histogram of an atrophic tongue is shown at bottom left (referenced black X). The X axis of the graph depicts the A color channel value, and the Y axis depicts the number of pixels having that value. In the atrophic tongue, approximately 150 pixels have a redness value of 175, and approximately 10 pixels have a redness value of 160.

In the "average red" determination, the average value of redness (measured in the A channel) in the AOI is determined, and can be compared between two images. In the "average blue" determination, the average value of blueness (measured in the B channel) in the AOI is determined.

The median of a predetermined LAB channel can be measured, and the value of the median can be compared between two images.

The minimal and maximal values in a predetermined LAB channel can be measured, and these minimal and maximal values can be compared between two images.

The size and shape of the lesion can be measured as well, by detecting the area of the lesion, the equivalent diameter, and the major axis length. These aspects of the lesion are especially important in evaluating ulcerations such as apotheosis, vesiculoulcerative lesions, carcinoma or malignant lesions, infections, burns, as well as non-ulcerative lesions such as pigmented lesions or white lesions.

Referring to FIG. 1, the right-hand panel 30 shows the results of calculations of the color information attributes described above, for the atrophic tongue (column 32, second from left), as compared with the normal region of the tongue (column 34 second from right). A numerical comparison between the two appears in the right-most column 36. In certain rows of the left-most column, two color information attributes are displayed side by side on a single line, for technical reasons.

Thus, in the $5^{th}$ row, "average red/blue" 38 displays the average red value next to the average blue value in the AOI. (There is no mathematical computation between the average red and the average blue, and the ratio is not calculated, rather the two values are merely displayed side by side). Similarly, the minimal red value and the maximal red value appear on a single line 39 (row 6), the minimal blue value and the maximal blue value appear on a single line 41 (row 7), and the median red value and the median blue value appear on a single line 43 (row 8).

Medical practitioners familiar with the invention can appreciate the diagnostic significance of these numerical results and can use them to determine the future treatment course.

Figure 2:
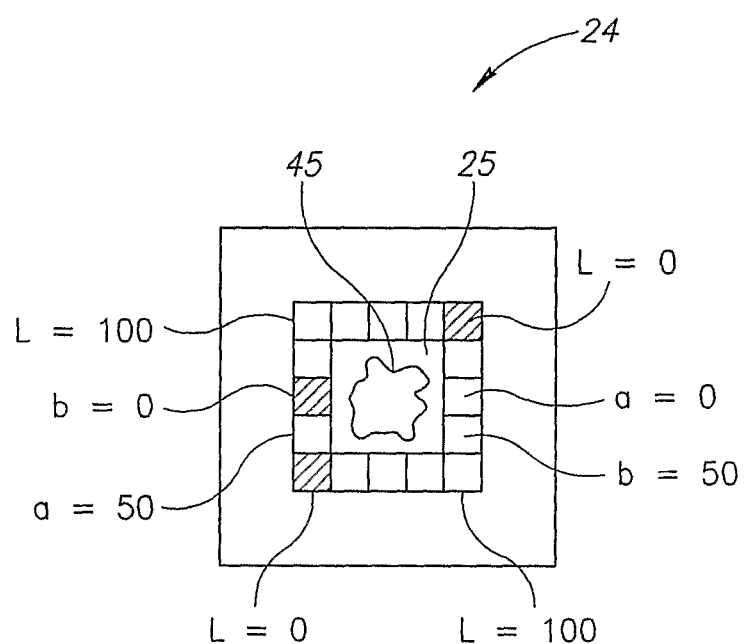
FIG. 2 is a preferred embodiment of a reference label for use with the invention.

In a preferred embodiment, shown in FIG. 2, the reference label 24 has a window cut in it, and is placed around the lesion 45 so that the lesion 45 appears in the window, with the reference colors surrounding the lesion. This will bring the reference colors in close proximity to the lesion. Preferable values of reference colors on the reference label are L=100, L=0, A=50, A=0, B=50, B=0. These have been found to be most suited for images of the human body. The label can be adjusted to a suitable size for the area of interest to be analyzed.

By examining the four sides of the window 25 of reference label 24, and evaluating the color intensities on all four sides, a clear indication can be obtained of the level of homogeneity of the illumination during the image capture activity. If the homogeneity is not sufficient, the image is not suitable for analysis. In addition, the system enables adjustment of minor gradients in illumination to improve homogeneity. These two features provide an additional level of quality assurance in image analysis, and a lower level of dependency of the illumination quality.

Figure 3A:
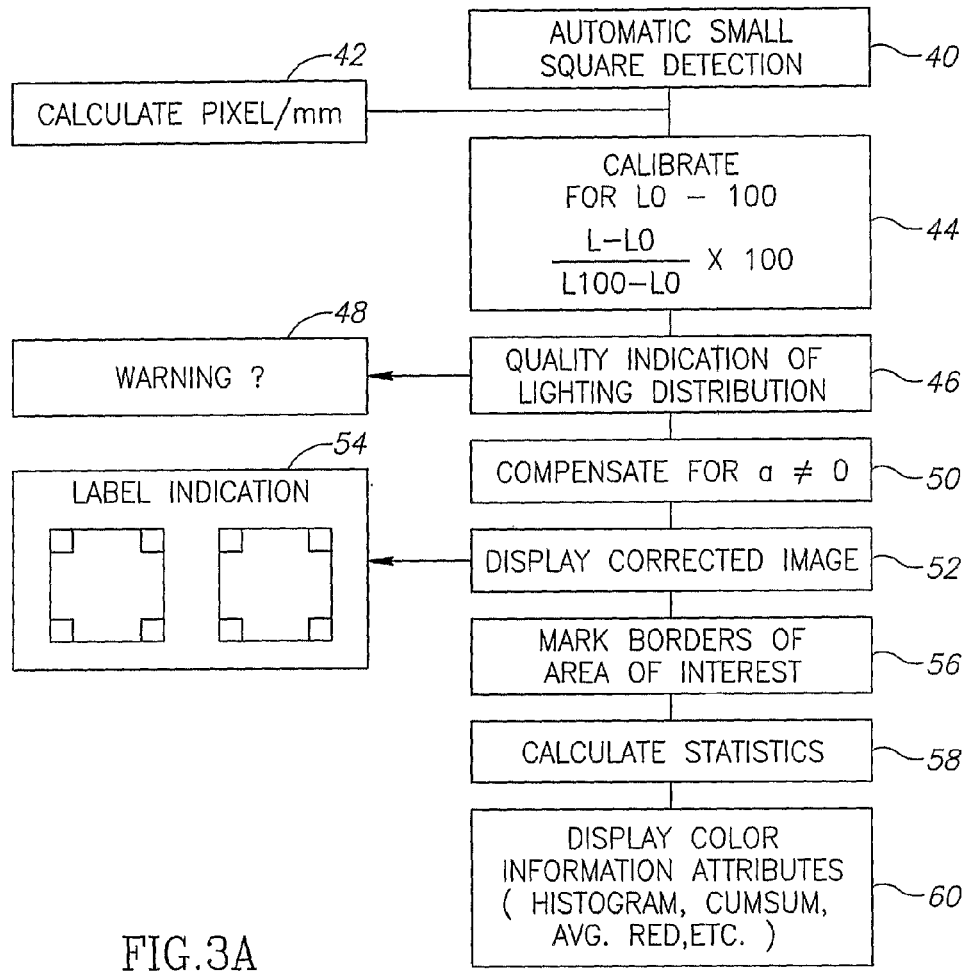
FIGS. 3*a-b* show respectively, a flow chart depicting preferred steps for activation of the method, and a preferred embodiment of the system of the invention.

Referring to FIG. 3a, a flow chart is shown detailing preferred steps for implementation of the method and system of the invention. The software implementation is straightforward and was programmed using the MATLAB software package (available from Mathworks Inc., Natick, Mass.), in particular the image processing toolbox.

Once a digital image has been captured and transferred to a computer station containing the software of the invention, analysis can be initiated as follows. Preferably, the software can perform automatic detection of the reference label 24 and of the reference colors upon it, using a search detection algorithm. In block 40, automatic small square detection is performed to recognize the reference colors upon the reference label.

Optionally, the number of pixels/mm upon the entire reference label 24 or upon the individual reference colors, is calculated (block 42), to give an indication whether the image was captured from too far a distance. If this were indeed the case, the analysis would be inaccurate and unsuccessful, since the resolution of such an image is poor; therefore the analysis is terminated when too few pixels/mm are measured, and a termination message is displayed.

In block 44, the color calibration of the L channel is performed (block 44). Since each reference color is larger than a single pixel, the LAB color value of several of these pixels within each reference color is determined, then averaged to create an average measured value of the reference color. This averaged measured value is then compared to the true value, and the image can be corrected for any color distortion. Use of an averaged measurement signifies that the detection of whether a distortion exists in the color, does not rely on a single dot or pixel.

Preferably, after an averaged measured value is made for a single specific reference color, such as measurement of the average black ($L_0$), when (L) represents the true value of the reference black, calculation for detection of the distortion is performed using the calculation:

$$\frac{L - L_0}{L_{100} - L_0} \times 100$$

In block 46, a quality control step is performed to detect the existence of lighting "streaks", or variations within different sections of the image. In the preferred embodiment of the reference label used, two distinct squares of each reference color are included in the label. The average measured value of the pixels within each of these two distinct squares is calculated, and if a significant difference (such as over 10%) is noted between the average measured values of the two squares, the lighting is significantly varied within different areas of the image, and calibration cannot be performed. A warning is then displayed (block 48), and the analysis is aborted. If quality control indicates that the variation between the two reference squares is not significant, the analysis proceeds to block 50.

In block 50, the other reference colors are calibrated similarly to the L channel calibration described, and the image will be corrected in each of the LAB channels, based on the distortions measured. For instance, if reference values of L=100, L=0, A=50, A=0, B=50, B=0 are used, the average measured value of $A_{50}$ is calculated, and compared to its true value using the following calculation (with (A) representing the true value of the reference at redness A=50):

$$\frac{A - A_{50}}{A_{50} - A_0} \times 50$$

The corrected image is then displayed in block 52. Optionally, in block 54, two images of the reference label are displayed side by side, with one image displaying the label before calibration, and a second image displaying the label after calibration. This allows a visualization of the extent of color correction that was performed.

In block 56, the user selects the borders of the area of interest on screen, by manual manipulation of the mouse or using the keyboard to move along the image and create an outline on screen.

In block 58, the color information attributes are calculated, and displayed on screen (block 60). These can include a cumsum value, a threshold analysis, a histogram of a single LAB channel, the average color value measured in a predetermined LAB channel, the median of a predetermined LAB channel, the minimum color value measured in a predetermined LAB color channel, or the maximum color value measured in a predetermined LAB color channel.

Additionally, size and shape information can be calculated and displayed. For instance, the relative magnification, the equivalent diameter, and the length of the major axis can be calculated.

Calculations and comparisons can be performed for several images present in the memory, to allow monitoring of a lesion over several months or years. A database can be created containing relevant information for each patient, easing retrieval and analysis of images, statistics and notes on each patient.

Figure 3B:
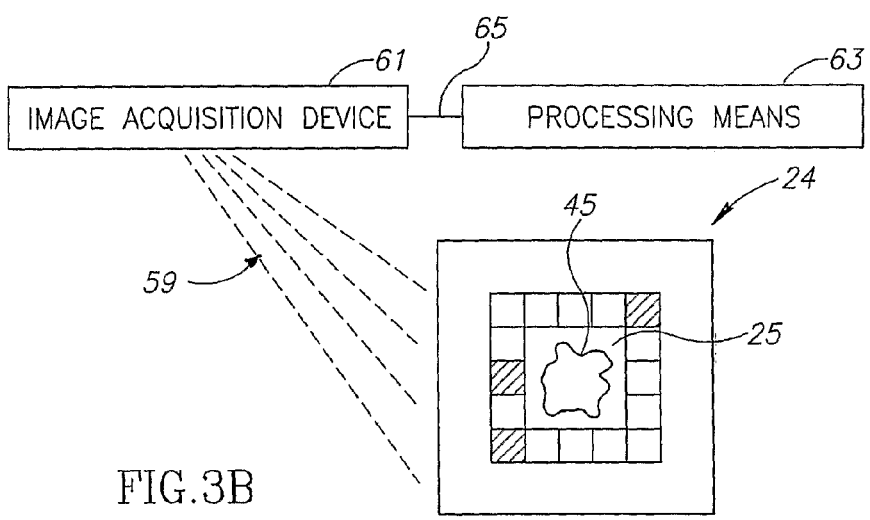

Referring to FIG. 3b, there is shown a block diagram of the system for use with the method of the invention. The system comprises an image acquisition device 61 such as a digital camera, or scanning means for converting image information into digital image information.

Preferably, a digital camera is used. Preferably, the digital camera has a memory of 3 MB. Preferably, the minimal resolution of the image is such that an area whose true size in reality is 3-5 $mm^2$ will contain 100 pixels in the captured image. The digital camera may provide flash illumination 59 of reference label 24, or other illumination means can be provided in a laboratory or clinic, which the patient visits.

If an optical film-based photo is used, and then converted into a digital image using a flatbed scanner, image conversion needs to be performed using the scanner-operating software, and preferably using photo-enhancing software such as Photoshop™ by Adobe Ltd., or Paintshop Pro™ by Correl Ltd.

In the system for use with the invention, a processing means 63 such as a personal computer can be used, featuring hardware having minimally a 256 MB RAM memory, a 1 GB Hard disc, and a high speed processor such as a Pentium 3 (Intel trademark) or higher. Standard computer peripherals are required, including a mouse, a keyboard and a color display screen.

The system requires few and inexpensive components, almost all of which are household items. The reference label 24 can be reasonably priced by being made for instance from paper having an adhesive on its underside. A practitioner interested in using the invention need only acquire calibration labels for placement near the lesion, and have a digital camera in his possession for capturing the image. If the digital image is transmitted to a central diagnosis center, the physician himself need not purchase the software.

In order to allow the invention to assist medical practitioners located in a widespread area, images captured by individual practitioners or even by patients themselves, can be sent in a digital format via a communications link 65 to a central analysis and diagnostic center, where the processing means 63 can be installed. The digital formal of the image can also be provided in a portable digitally-recordable medium, such as a disc on key, or CD, etc. The color calibration can be performed at the diagnostic center, and an analysis of the color information attributes, along with an evaluation of their relevance to the diagnosis, can be returned to the practitioner or patient.

Using modern communication means, such as the Internet for transmission of the images, the analysis can be performed and its conclusions can be conveyed to the practitioner in a matter of minutes. This type of "telemedicine" can allow relatively immobile or inaccessible patients to virtually receive the opinion of a specialist at a reasonable cost.

In some clinical instances, staining of the tissue is performed before placement of the reference label upon the tissue. Different tissues absorb stain to a different degree, for instance certain malignant and pre-malignant tissues absorb considerably more toluidine blue dye than normal tissue tends to absorb. The dye is applied to the tissue for several minutes then the tissue is washed to remove the excess. Retention of dye indicates a dysplastic or malignant tissue.

In order to determine the extent of staining and therefore the medical significance to the probable diagnosis and treatment, the reference label 24 can then be applied to the tissue after staining, and a digital image can be captured for computerized analysis using the method of the invention. The computerized analysis is far more objective and informative than the prior method of visualization using the naked eye. Areas having the most intense degree of staining can be detected and if necessary, can be selected for biopsy, as they give an indication of the most appropriate area to be incised.

In or upon the human body, lesions of various colors may appear which need to be monitored for changes in size and appearance, and upon which analysis of the color should be performed. Redness, also termed "erythema", can signify malignancy, infection or inflammation. Redness results from dilation and congestion of superficial capillaries, and is an important sign in several pathologic conditions. Redness signaling inflammation, can indicate:

1. Infection: either local infection, such as for instance an abscess or gingivitis in the oral cavity. Alternatively, a diffused infection may be present, such as cellulitis. A diffused infection can nevertheless have symptoms of redness. The microorganismic infecting agent of a local or diffused infection may be bacterial, viral or fungal. Examples of infecting agents that result in measurable redness are viral infection such as recurrent herpes, or fungal infection such as candidiasis.
2. Reactive lesions, due to common irritants (e.g. smoking) may give measurable redness.
3. Immunological conditions, such as auto immune diseases or allergic reactions (e.g. contact stomatitis) as well as dermatoses (e.g. Lichen Planus) may give measurable redness.
4. Deficiencies such as vitamin B12 deficiency and anemia.

The degree of the erythema in the aforementioned medical conditions correlates the severity of the inflammation, therefore measuring the degree of redness can aid in determining the activity level of the disease, the extent of healing or the presence of an adverse reaction to the treatment. Changes in the size and shape of the borders of the erythematosus area can indicate deterioration or improvement of the medical condition.

In addition to inflammation, redness or other color changes in the tissue can signal the presence of a malignancy. These changes can be followed using the invention, in order to determine whether color changes occurred over time, and whether they are significant enough to warrant treatment.

Oral cancer for instance, which has variable clinical features, can present clinically as a red or a white lesion, an ulcerated lesion, or an elevated outgrowing mass with irregular surfaces. Premalignant lesions, such as erythroplakia, appear as reddened (erythematosus) areas, and biopsies of these lesions reveal that 90% are malignant or premalignant (dysplastic, namely, have the potential to become malignant and require continued observation to rule out the presence of enlargement or color changes).

Dermal lesions that become more intensely brown, or more intensely gray, can signify melanoma.

Analysis can be performed on images originating from any tissue or organ of the human body. Tissues that are easily accessible for image capture, using relatively non-invasive procedures include the epidermis, the gastrointestinal tract, the female reproductive tract, and the oral cavity and its internal structures including the teeth. Internal organs of the human body can be photographed in invasive surgery, preferably after a reference label is included in the image or a calibration device is used, and analysis results of the color intensity and distribution within a tissue or organ, can be received within minutes after the image is captured. This can assist in making surgical decisions.

Analysis can be performed on the surfaces of the tooth. The degree of discoloration of the tooth can be evaluated using the invention. Discoloration can result from decay, demineralization, early childhood drug use, congenital defects, or exogenous staining (due to drinking or smoking). Decalcification and hypocalcification occurring over time can create a lighter or whiter color of the tooth surface, and decay can appear brown, yellow or gray. The color of an entire tooth can change to a yellow or brown, due to pathological conditions, to dentinal deposition after trauma or following dental treatment such as root filling. The extent of any of these color changes upon the tooth can be evaluated, in order to determine the course of treatment.

EXAMPLES

Referring to FIG. 4, a digital image was captured of a white dysplastic (premalignant) lesion. Note reference label 24 having reference colors, placed adjacent to the lesion 64 before the image was captured. In the left-most panel (referenced "X"), the area of interest selected comprises the lesion. The borders of the lesion have been traced onscreen, and appear with a faint blue outline 66. In the panel referenced "Y", the digital image is identical, however the area of interest selected comprises normal tissue (faint blue outline 68 above the lesion). Color analysis thus allows comparison between the normal tissue and the lesion.

Note histogram 70, 72 pertaining to each panel, appearing at bottom left. The color information attributes calculated appear in panel 74 at right, with the results pertaining to the lesion in column 76 (second from the left), and the results pertaining to normal tissue in column 78 (second from the right). A numerical comparison of the lesion and normal tissue appears in column 80 (at far right).

Figure 5:
FIG. 5 depicts two digital images of a lip carcinoma, with a two-month interval elapsing between the images, with a depiction of the results of the analysis.

Referring to FIG. 5, a carcinoma of the lip was examined and an image was captured (panel Y). At a second visit (panel X), the size of the lesion had grown. In both images, the AOI selected (surrounded by a faint blue line 82) was the lesion. The histogram cumsum 84, (shown in the bottom of the right-hand panel), is similar in value, and being a weighted histogram, is especially reliable in indicating similar color for the lesion at both visits.

Figure 6:
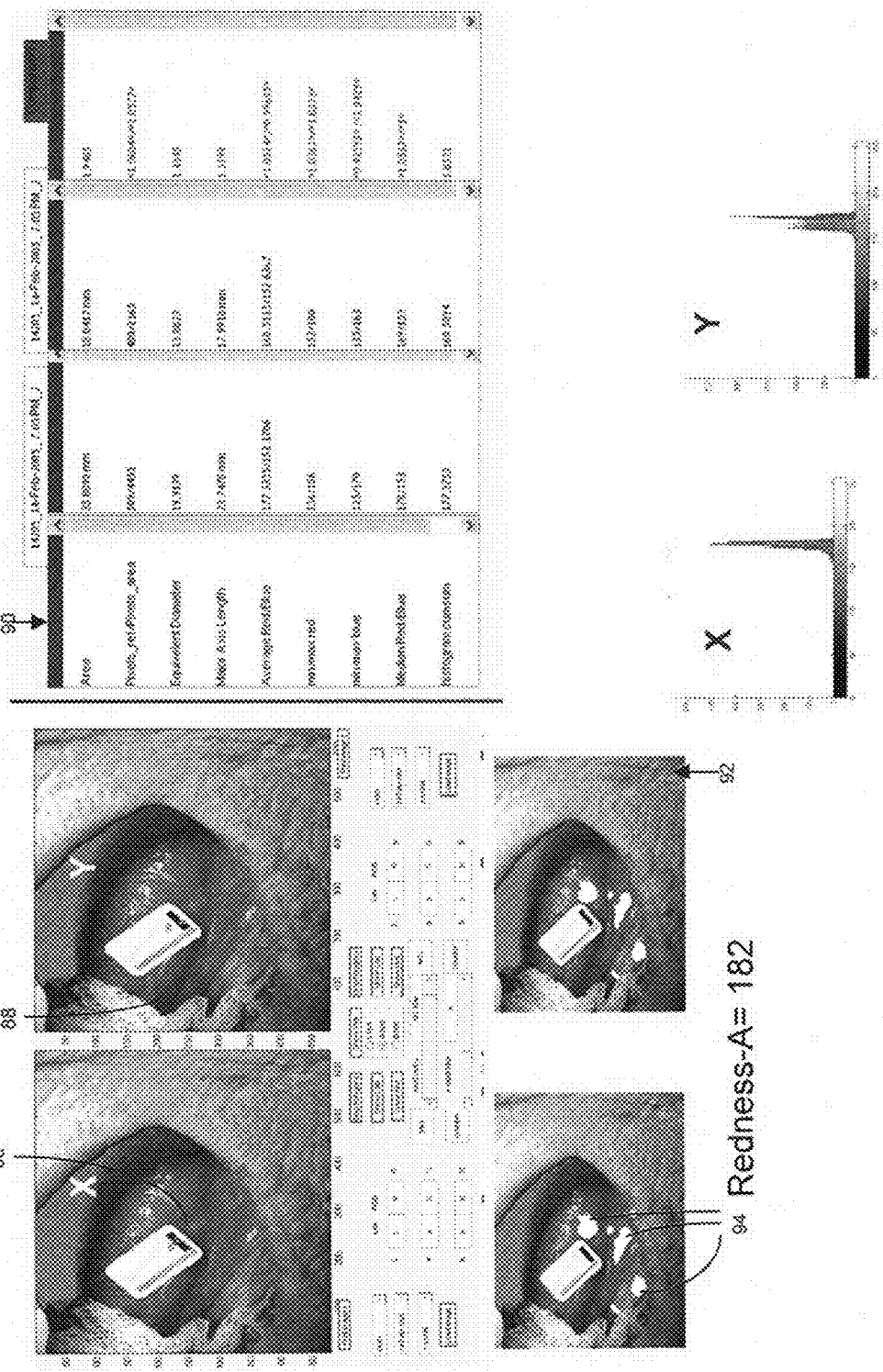
FIG. 6 depicts several digital images of a premalignant lesion of the tongue, threshold analysis upon the image, and additional color information analysis results.

Referring to FIG. 6, premalignant erythroleukoplakia of the tongue is shown. In the digital image at left (referenced X), the premalignant area has been selected in the AOI 86. In the image at right (referenced Y), normal tissue has been selected (faint rectangle 88 at left). Color information attributes were calculated, and appear in the right panel 90. A threshold analysis was performed on the image, and the pixels having a color value higher than or equal to A=182 appear highlighted 94 in the image 92 (bottom left panel).

Figure 7:
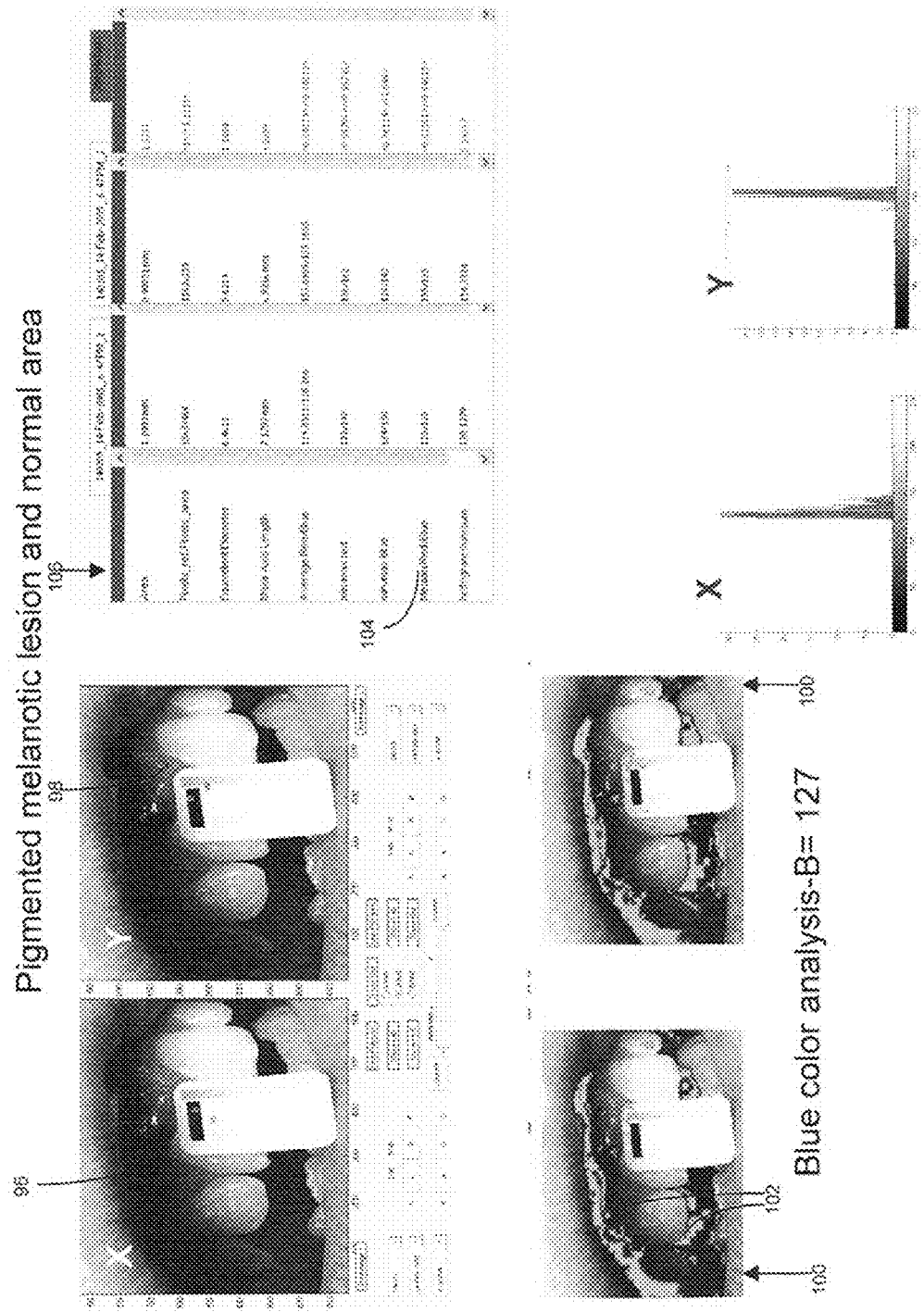
FIG. 7 depicts digital images of a pigmented melanotic lesion, threshold analysis upon the image, and additional analysis results.

Referring to FIG. 7, a digital image of a pigmented melanotic lesion of the gingiva is shown. In the right panel (referenced Y), the dark circular lesion has been selected as the AOI 96. In the panel referenced Y, normal gingival tissue has been selected as the AOI 98 (faint blue circle in upper right side of image). Since the lesion is pigmented, the blue channel of LAB is most relevant to the analysis, and has been chosen for threshold analysis 100. Pixels having B>=127 are shown as highlighted areas 102 on the screen. Additionally of interest to the analysis in this case (and in dark lesions) are comparisons between healthy and lesion tissue, in both the blue and red channel, such as for instance, the median red 104 and the median blue 104, shown among the color information attributes in the right-most panel 106.

Figure 8:
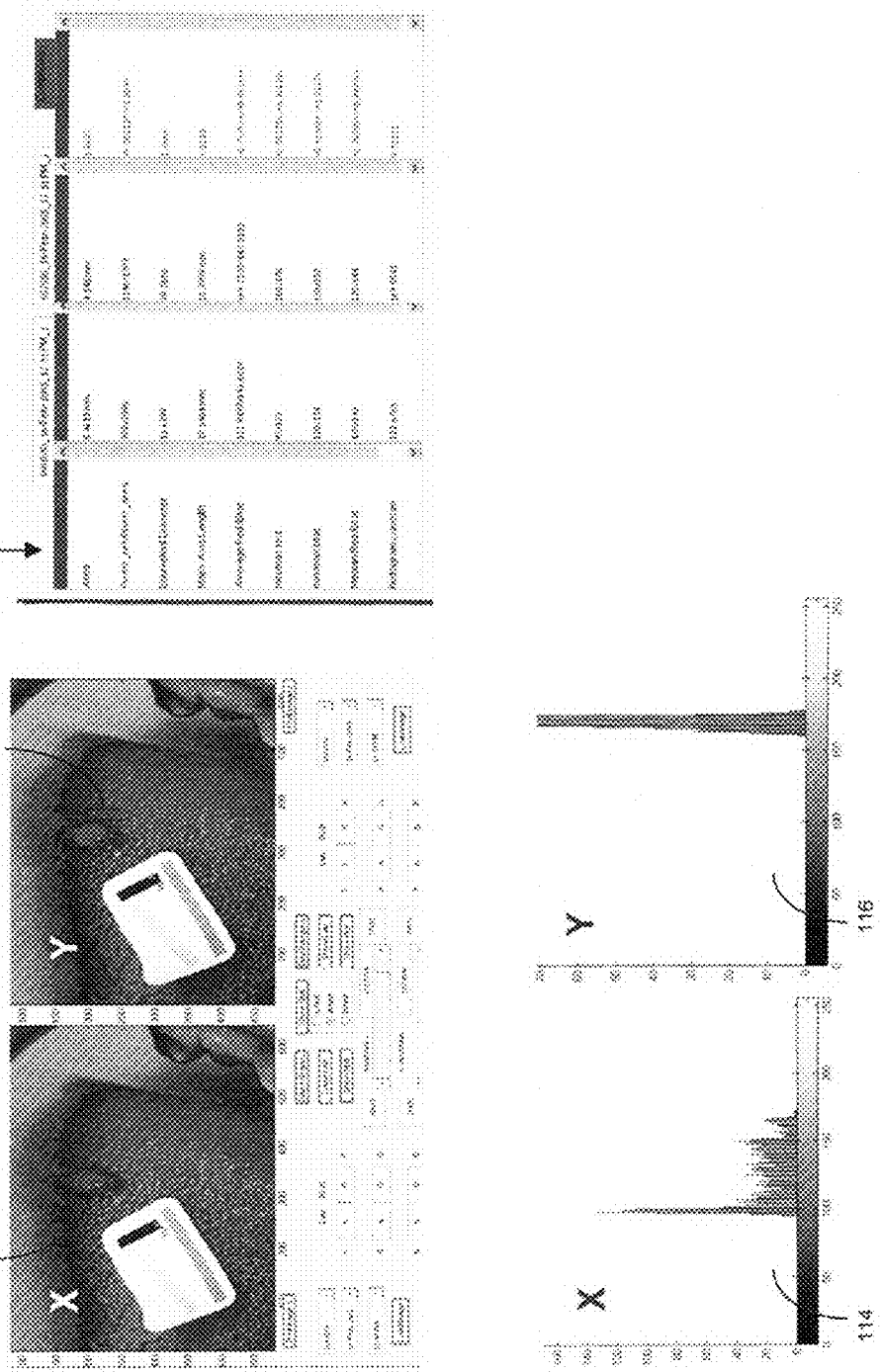
FIG. 8 depicts digital images of a vascular tumor, and color information attribute results.

Referring to FIG. 8, a vascular tumor (hemangioma) is shown in the digital image. In the image referenced X at left, the AOI 108 selected contained the tumor, while in the image referenced Y, normal tissue was selected as the AOI 110

(outlined in blue). Color information attributes appear in panel 112 at right, with the histograms 114, 116 appearing at bottom left. The histograms 114, 116 depict vastly different coloration in the tumor as opposed to the normal tissue.

Figure 9:
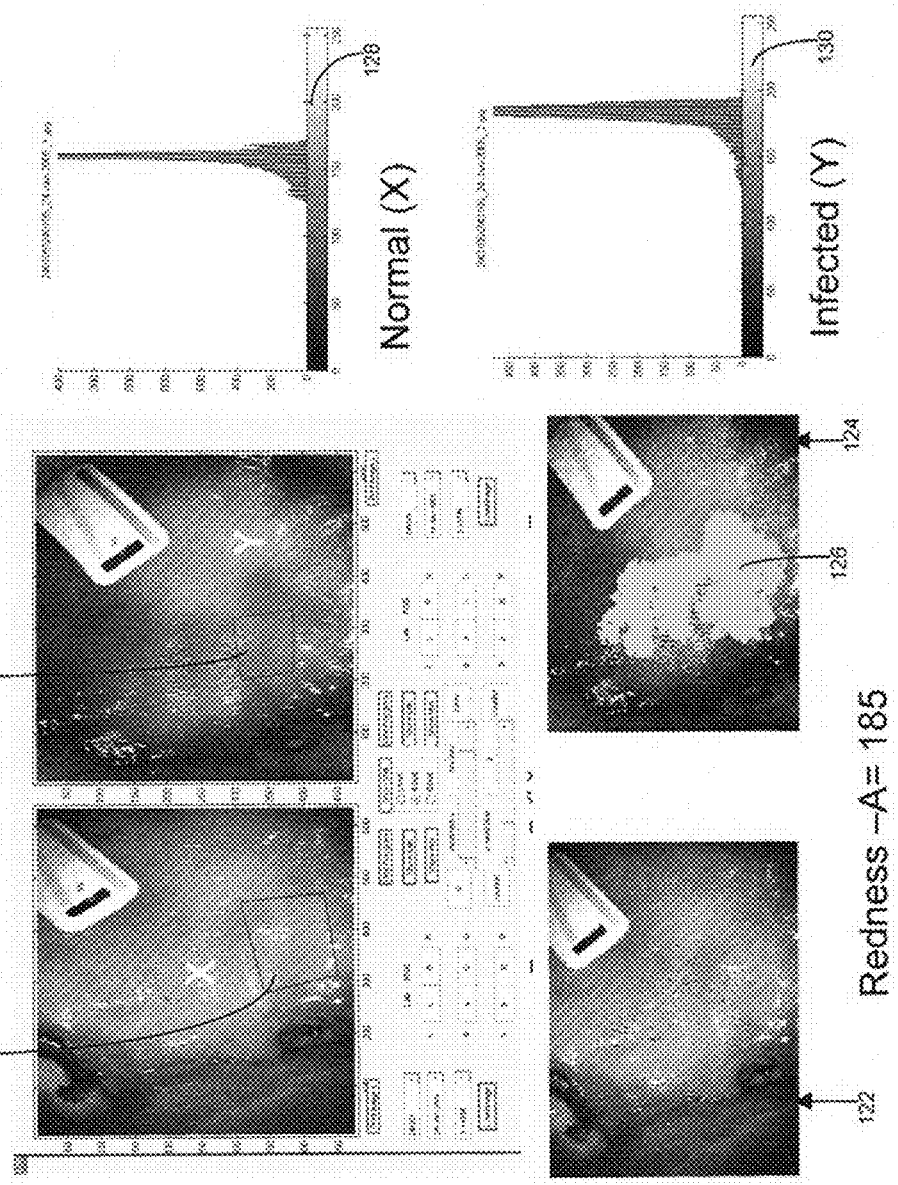
FIG. 9 depicts digital images taken before and after treatment of a fungal infection in the oral palate, threshold analysis upon the image, and the histogram results.

Referring to FIG. 9, digital images of a fungal candidial infection of the palate were captured at two different visits. At right (referenced Y), the AOI 118 selected includes infected areas that appear reddened. At left (referenced X), a similar area 120 was selected on a subsequent visit after treatment was administered. In the threshold analysis images 122, 124 appearing at bottom left, areas having a redness value of A>=185 are highlighted on screen 126. The threshold analysis clearly shows vast improvement, since redness intensity has diminished at the subsequent visit (image 122), with no pixels whatsoever measured above or equal to the threshold value (A=185). Histograms 128, 130 show the majority of pixels having a color value of A=160 after treatment (X histogram, 128) while the majority of pixels having a color value of A=190 before treatment (Y histogram, 130).

Figure 10:
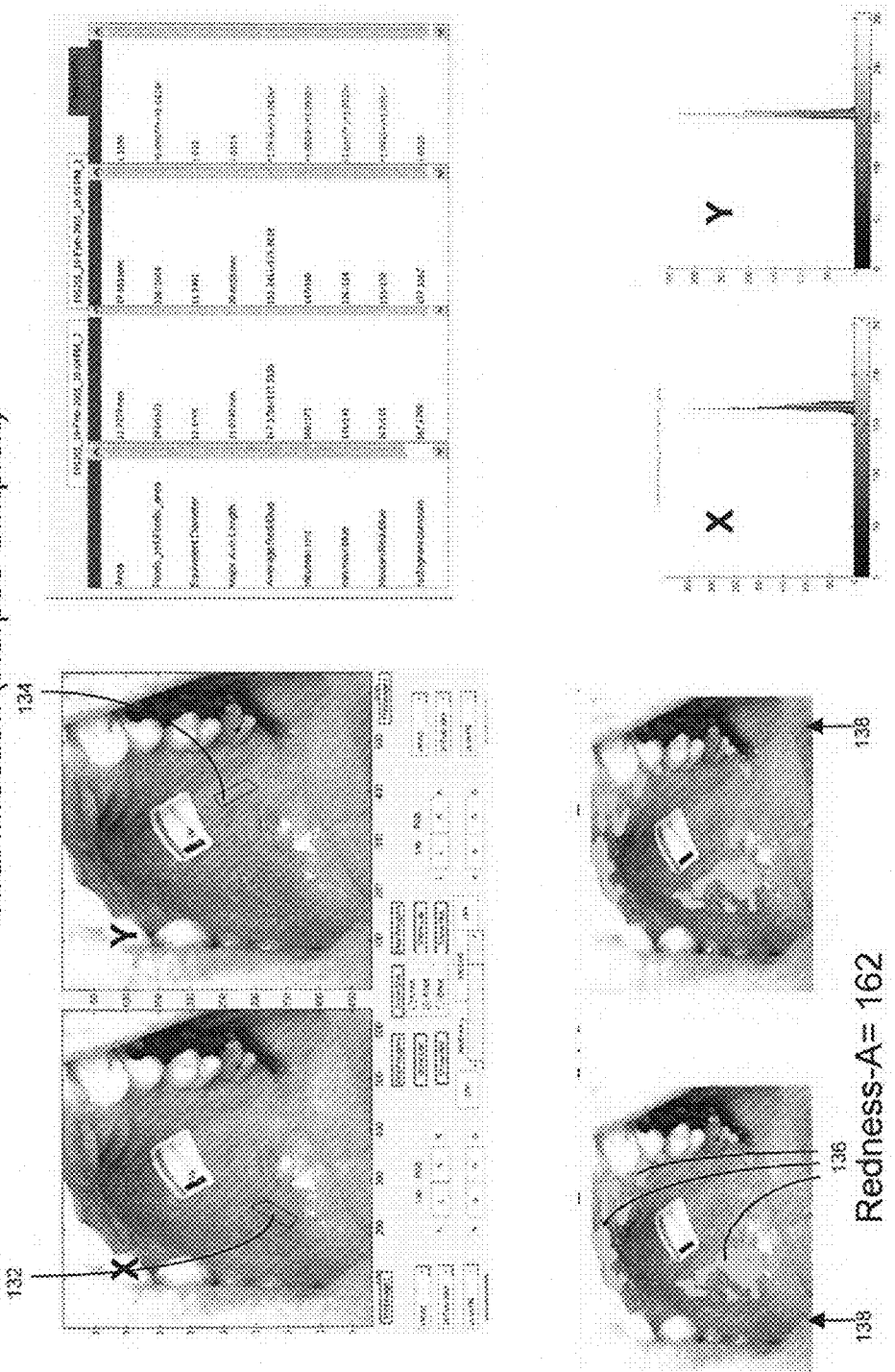
FIG. 10 depicts digital images of a viral infection in the oral cavity, threshold analysis upon the image, and additional color information analysis results.

Referring to FIG. 10, digital images of a viral infection of herpes simplex are shown. In panel X (at left), infected areas were selected as the AOI 132, while in panel Y (at right), a normal healthy area 134 was selected. The threshold analysis in this case assists in mapping the infected area, which is highly relevant to the diagnosis. The pattern of infection is two-sided, as seen clearly in the highlighted areas 136 of the threshold analysis images 138, matching that of a Herpes Simplex I infection, as opposed to a Herpes Zoster infection, which usually involves a single side of the palate or the face (=unilateral).

Figure 11:
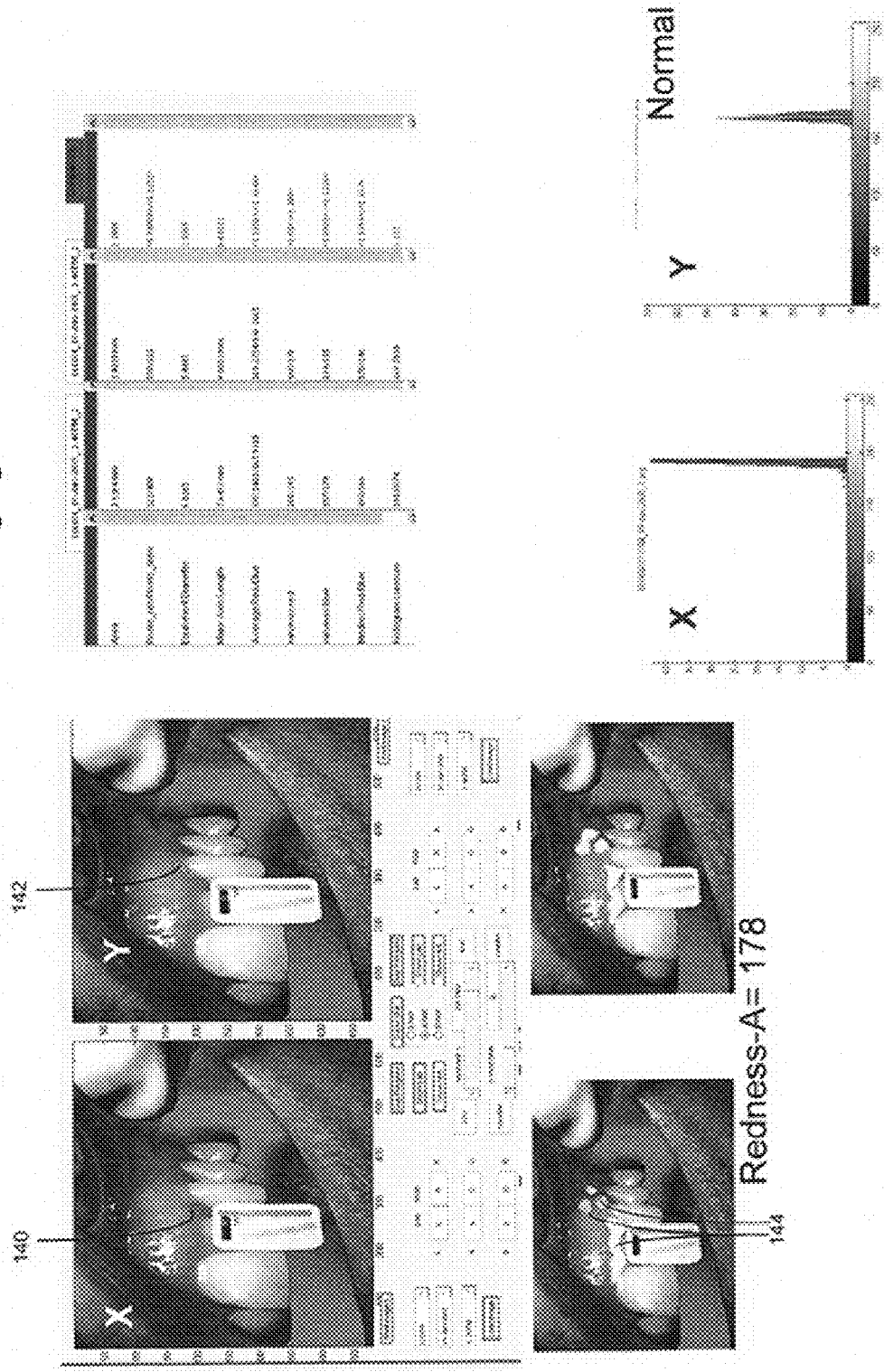
FIG. 11 depicts digital images of an oral Lichen planus infection of the gingiva, threshold analysis upon the image, and additional color information analysis results.

Referring to FIG. 11, an infection of Lichen Planus in the gingiva was analyzed, and compared to normal tissue. The infected area selected as the AOI 140 in the left image (referenced X) does not appear to the naked eye to be significantly more red than the normal tissue selected as the AOI 142 in the image referenced Y. However, threshold analysis with a redness value of A=>178 clearly shows areas 144 which are more reddened.

Figure 12:
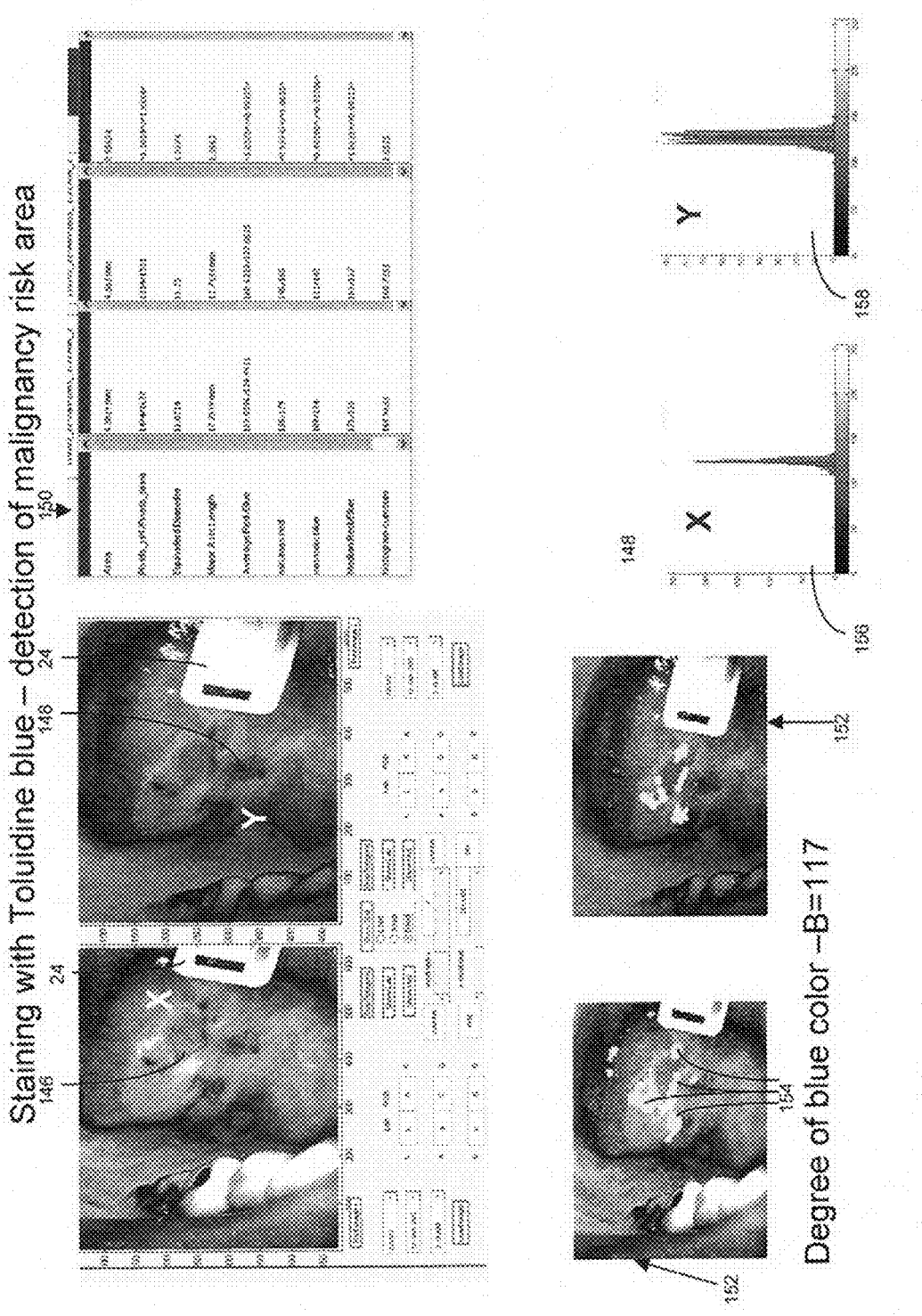
FIG. 12 depicts digital images of the oral cavity after staining with toluidine blue, for detection of malignancies, with a depiction of threshold analysis as well as additional analysis results.

Referring to FIG. 12, staining with toluidine blue was performed on the tissue, then the reference label 24 was placed on the tissue, and the image was captured for analysis. In the image referenced X, the AOI 146 selected was a normal area, with no retention of stain in the tissue. In the image referenced Y, the AOI 148 selected appeared blue after staining. Color information attributes were calculated for each area, and appear generally in the panel 150 at right.

The threshold analysis images 152 appearing at bottom left, highlights areas 154 having a color value in the B channel of B=>117, and allows the physician to determine which regions are more intensely stained and are therefore prime candidates for biopsy. Histograms 156, 158 appearing at bottom right graphically depict the difference in coloration between the normal tissue AOI versus the stain-retaining AOI.

Figure 13:
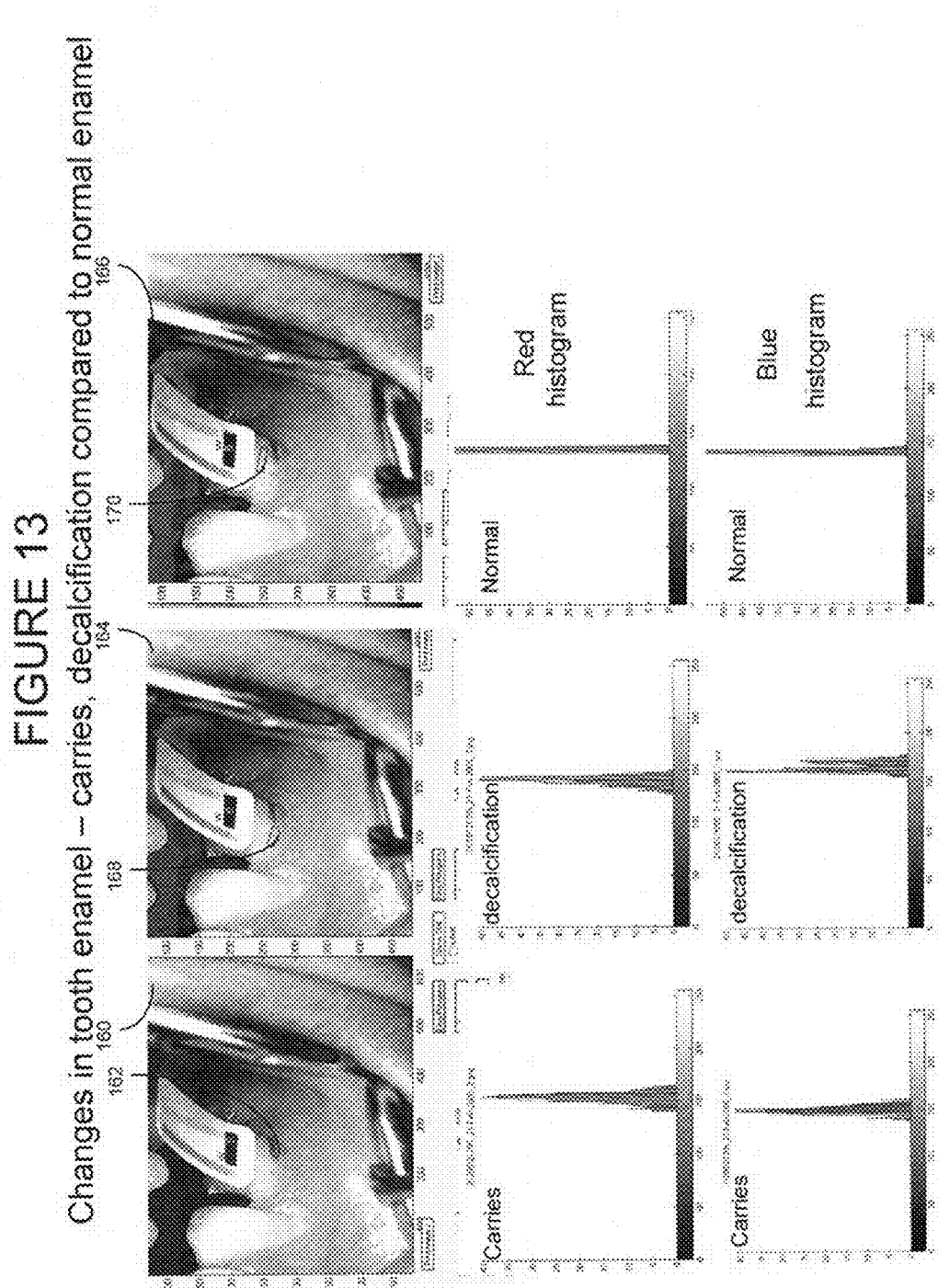
FIG. 13 depicts digital images of the teeth, upon which analysis of changes in the coloration was performed, with results of the analysis shown.

Referring to FIG. 13, variations in the coloration of tooth enamel were analyzed. In image 160 at left, an area representing caries was selected as the AOI 162. In image 164 at center, a decalcified region was selected as the AOI 168, and at right 166, a normal area of tooth 170 was selected. Color information attributes were calculated. The respective histograms in both the red channel (center row), and the blue channel (bottom row) are shown below each image. The analysis allows changes to be detected over time, to determine whether they need to be treated.

Figure 14:
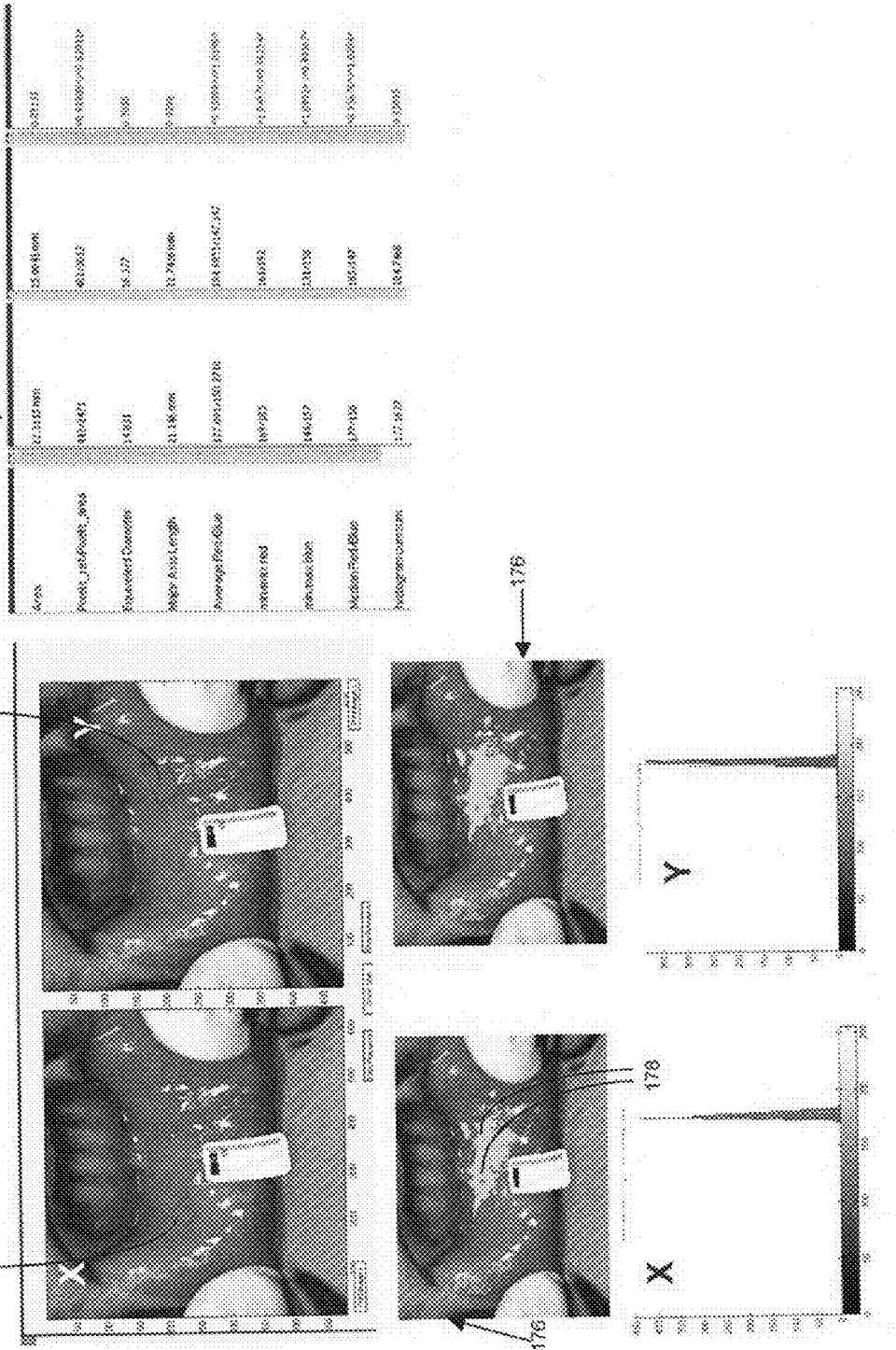
FIG. 14 depicts digital images of granulomatous disease manifested as a swollen lip with a depiction of threshold analysis as well as additional analysis results.

Referring to FIG. 14, granulomatous disease is shown in an image of a swollen lip. Normal tissue was selected as the AOI 172 in image X at left, and reddened tissue was selected as the AOI 174 in image Y at right. Color information attributes were calculated, among these a threshold analysis 176 appears at left (central row), where intensely reddened areas 178 are highlighted on screen.

Figure 15:
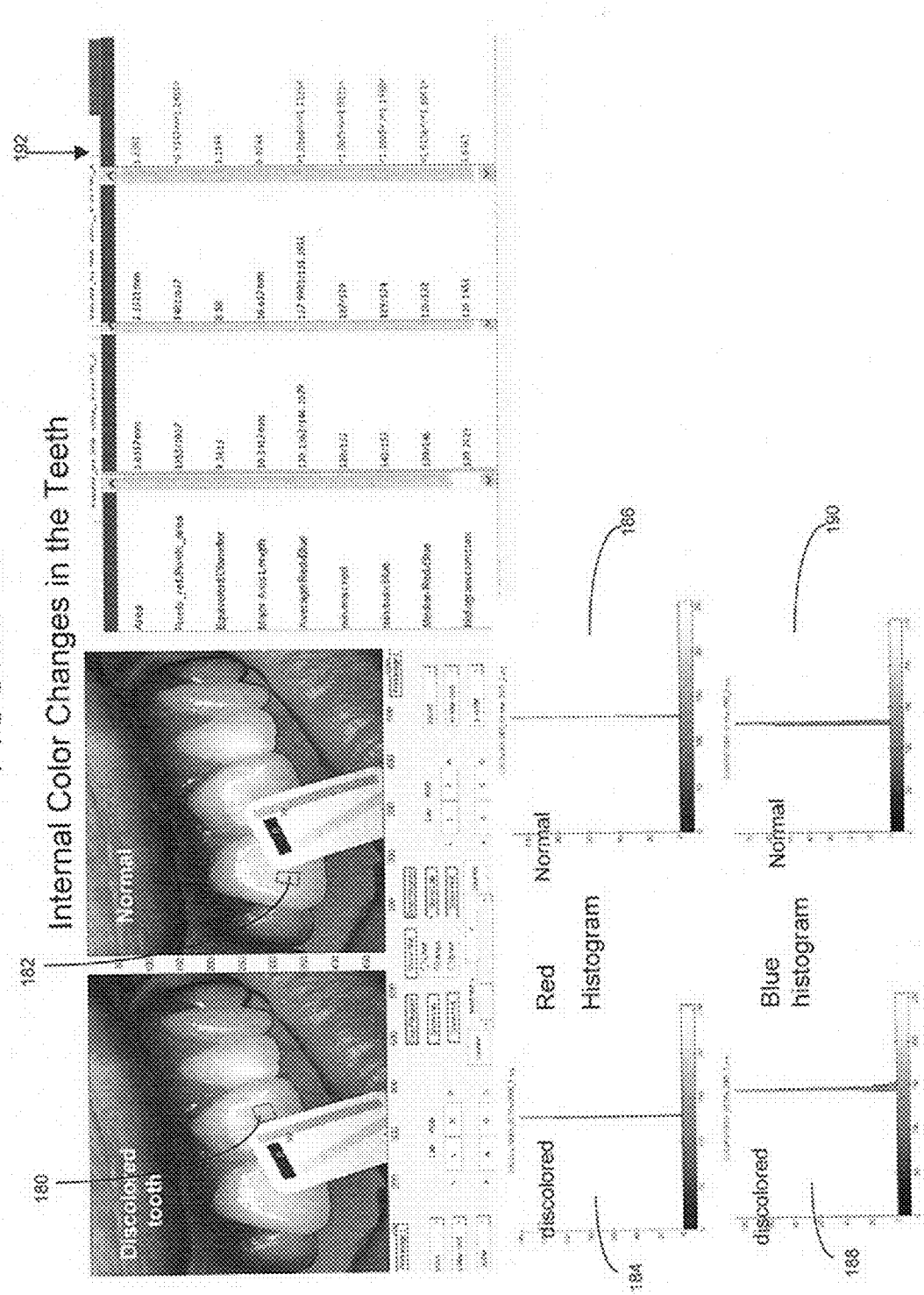
FIG. 15 depicts digital images of teeth, in which a single tooth has undergone a color change, with results of the analysis shown.

Referring to FIG. 15, internal color changes have occurred in a single tooth. An area on the discolored tooth was selected as the AOI 180 in the image at left, and an area on a normal colored tooth was selected as the AOI 182 in the image at right. The histograms of the discolored tooth 184 and the normal tooth 186, in the red channel, are displayed below the images, as are the histograms in the blue channel 188, 190. Additional color information attributes are displayed in panel 192 at right. Evaluation of the degree of discoloration is important for aesthetic and medical diagnosis and treatment.

In the following Examples, and their associated FIGS. 16-21, clinical images of three groups of diseases were evaluated in order to statistically assess the success rate of the invention in tracking and evaluating the clinical significance of the measured color information attributes. The groups of diseases selected represent major pathological processes, namely infection, inflammation and premalignancy.

Referring to FIGS. 16A, 17B, 19B, in the left-most image, infected tissue was selected as the AOI (area of interest), and marked with white arrows, while in the right-most image, normal tissue was selected as the AOI, and marked with black arrows.

The color information attributes were calculated for each of these AOI, see for instance, FIGS. 16C, 19C.

For each individual patient, the ratio was determined for the median red color value in the patient's normal tissue, versus the median red color value of diseased tissue. This ratio was then calculated for all patients suffering from the same disease, forming a disease group. This parameter was assumed and proven to follow a normal statistical distribution. Every group has its own particular average and standard deviation (mean and sigma) as shown in the normal distribution curves at the left side of the panels in FIGS. 16B, 17A, 18, 19A.

In the right panels, seen in FIGS. 16B, 17A, 18, 19A, the normal probability distribution for a plurality of individuals is illustrated as a linear straight line. The results measured for each specific patient tested, are depicted as "+" signs. Ideally, all signs should align with the linear straight line indicated, though a certain degree of variance is expected.

These normal distribution curves allow visualization of the average and standard deviation of the ratio of the median red color of the patient's normal tissue, vs. the median red color of the diseased tissue, for a plurality of patients having a similar condition. Thus, these normal distribution curves allow a determination of the stage of the disease. A normal patient not suffering from any disease would have a ratio equal to one. A certainty window of 0.05 will have a red ratio of 0.95-1.05.

In these normal distribution curves, (left sides of panels in FIGS. 16B, 17A, 18, 19A), the number value displayed in the box at the pinnacle of the curve, signifies the error probability fit to the certainty window value. The certainty window is calculated by measuring the area under the curve, as compared to the entire area of the plot. For example, if the certainty value indicated in the certainty window is 0.05 and the value within the box is 0.04 the odds of having a mistake is 4%.

Thus, for every plot per disease, the measured parameter representing the ratio of the median red color of the patient's normal tissue, vs. the median red color of the diseased tissue, is a parameter which provides the medical practitioner with an indication of the stage of the disease. The closer it is to the value one, the closer the patient's condition is to a healthy condition. People suffering from the particular disease would tend to have the parameter value closer to the average value of the curve. As the situation improves, this parameter value decreases toward one The analysis depicted in FIGS. 16-21, shows that the median red ratio parameter can be very well approximated as having a normal distribution. The inventive system can provide a scale for the confidence level of determining the status of the disease by measuring color changes for the different pathological processes. The invention thus provides statistical correlation between the analysis results determined, and the clinical conclusions.

In conclusion, the various aspects of the entire invention allow quantification and mapping of coloration in digital images originating in human tissue. The invention can therefore be used as a computerized aid for analysis and follow-up of areas in or upon the body, in instances where the extent and degree of coloration is of interest. The invention allows analysis that is objective and is free of the optical errors which occur when the human eye is relied upon for color analysis.

Having described the invention with regard to certain specific embodiments thereof, it is to be understood that the description is not meant as a limitation, since further modifications may now suggest themselves to those skilled in the art, and it is intended to cover such modifications as fall within the scope of the appended claims.

The invention claimed is:

1. A method for computerized analysis of particular color changes of specific clinical nature for all types of medical analysis pertaining to color, present in one image originating from at least one lesion in human body tissue, comprising:
   a) placing a matching reference label having a plurality of reference colors, in the vicinity of every analyzed lesion, said reference label having a window cut in it and placed so as to surround the corresponding lesion size and shape associated with an area of interest (AOI) therein;
   b) capturing a color image including every analyzed lesion and the corresponding reference label along with human tissue encompassing said reference label, wherein said image is a digital image or is converted into a digital image;
   c) performing color calibration of the image using the LAB color system, said calibration comprising reading the color intensity value of at least one reference color from the reference label in the image, comparing said value to the true predetermined color intensity value of said reference color, and optionally correcting the digital data of the image in at least one channel within the LAB color system, for color distortion;
   d) selecting the borders of said AOI within the image;
   e) calculating the intensity and distribution of color within said area of interest in relation to said reference label using at least one channel of the LAB system, to give at least one color information attribute within a clinically relevant range; and
   f) displaying said at least one color information attribute upon display means;
   wherein at least steps (c) and (e) are performed by a processing means allowing color calibration and allowing calculation and display of said at least one color information attribute.

2. The method of claim 1 wherein an evaluation of the intensities of said reference colors on all sides of said window provides a clear indication of the level of homogeneity of illumination during said image capture activity.

3. The method of claim 1, wherein the calculation performed in step (e) for determining said at least one color information attribute is selected from at least one of the following: a cumsum value, a threshold analysis, a histogram of a single LAB channel, the average color value measured in a predetermined LAB channel, the median color value of a predetermined LAB channel, the minimum color value measured in a predetermined LAB color channel, and the maximum color value measured in a predetermined LAB color channel.

4. The method of claim 3, wherein said cumsum value is a weighted average of the color intensity in an area of interest, for calculating the most predominant color in said area of interest.

5. The method of claim 3, wherein said threshold analysis is comprised of selecting a value of color intensity, and providing an indication within said image, of pixels above or equal to said value of color intensity.

6. The method of claim 1, further comprising the steps of performing a calculation relating to the size and shape of the area of interest, and displaying the result of said calculation on display means; said calculation selected from at least one of the group consisting of: calculating the size, calculating the relative magnification, calculating the equivalent diameter, and calculating the length of the major axis.

7. The method of claim 1, further comprising the step of staining said every analyzed lesion, prior to step (a) of placement of the reference label.

8. The method of claim 1, wherein said analysis is performed on at least two images, and said calculated color information attributes of both of said images are displayed visually adjacent to one another, said two images representing images taken over time from a similar area of a single person, or said two images representing two different areas of interest of a single person.

9. The method of claim 1, wherein said images are received from a distant location, and are transmitted in a format having digital image information contained within, to a central diagnostic center capable of performing color calibration, and capable of calculating said at least one color information attribute and of interpreting its relevance.

10. The method of claim 1, further allowing mathematical comparison of said at least one calculated color information attribute, to a database of color information attributes determined from images captured from a plurality of people.

11. The method of claim 1 for use in instances in which the intensity of the color is related to progression or regression of a medical condition.

12. The method of claim 11, wherein said medical condition is selected from: micro-organismic infection, inflammation, benign neoplasms, malignant neoplasms, reactive lesions, autoimmune diseases, vesiculoulcerative lesions, allergic reactions, dermatoses, congenital deformities, ulcerations, granulomatous disease and nutritional deficiencies.

13. The method of claim 12, wherein said neoplasm is selected from erythroplakia, leukoplakia, leukemia, and white lesions; and wherein said micro-organismic infection is selected from herpetic infection, candidiasis, mucomycosis, leishmaniasis, abscesses, gingivitis, apotheosis, diffused infections; and wherein said autoimmune disease is selected from psoriasis, contact stomatitis, Lichen Planus, Pemphigus, wherein said granulomatous disease is selected from Melkersson-Rosental syndrome.

14. A system for computerized analysis of particular color changes of specific clinical nature for all types of medical analysis pertaining to color present in one image originating from at least one lesion in human body tissue, comprising:
   a. a digital camera, or scanning means for converting image information into digital image information;

b. a reference label having a plurality of reference colors, said reference label having a window cut in it and being placed so as to surround an area of interest (AOI) in said lesion image, wherein said lesion image includes human tissue encompassing said reference label;

c. calculation means for calculating the size and shape of said lesion; and d. processing means comprising a memory device, a driver and display means, wherein said processing means is in communication with said memory device, and is configured to:

i. perform color calibration of the image using the LAB color system, said calibration comprising reading the color intensity value of at least one reference color from the reference label in the image, comparing said value to the true predetermined color intensity value of said reference color, and optionally correcting the digital data of the image in at least one channel within the LAB color system, for color distortion;

ii. calculate the intensity and distribution of color within an area of interest using at least one channel of the LAB system, to give at least one color information attribute within a clinically relevant range; and iii. display said at least one color information attribute upon said display means.

15. The system of claim 14, wherein said calculation performed to give said at least one color information attribute, is selected from at least one of the following: a cumsum value, a threshold analysis, a histogram of a single LAB channel, the average color value measured in a predetermined LAB channel, the median color value of a predetermined LAB channel, the minimum color value measured in a predetermined LAB color channel, and the maximum color value measured in a predetermined LAB color channel.

16. The system of claim 14, wherein said processing means is further configured to perform automatic detection of the reference colors upon said reference label.

17. The system of claim 14, wherein the LAB values of the reference colors on said reference label are L=100, L=0, A=50, A=0, B=50, B=0.

18. The system of claim 14, further comprising communication interface means allowing access to a communication system, allowing receipt of images from a distant location, said images being transmitted in a format having digital image information contained within, wherein said communication interface means enables transmission of a medical diagnosis to said distant location.

19. A non-transitory computer readable storage medium comprising software capable of:

a) performing color calibration of an image using the LAB color system, said calibration comprising reading the color intensity value of at least one reference color from a reference label present in an image, comparing said value to the true predetermined color intensity value of said reference color, and optionally correcting the digital data of the image in at least one channel within the LAB color system, for color distortion;

b) calculating the intensity and distribution of color within a predetermined area of interest (AOI) within said image, wherein said reference label has a window cut in it and is placed so as to surround said AOI so that said reference label is in close proximity to said image, using at least one channel of the LAB system, to give at least one color information attribute within a clinically relevant range, wherein said image includes a region encompassing said reference label; and c) directing display of said at least one color information attribute upon display means.

20. The non-transitory computer readable storage medium according to claim 19, wherein said calculation performed to give said at least one color information attribute is selected from at least one of the following: a cumsum value, a threshold analysis, a histogram of a single LAB channel, the average color value measured in a predetermined LAB channel, the median of a predetermined LAB channel, the minimum color value measured in a predetermined LAB color channel, and the maximum color value measured in a predetermined LAB color channel.

21. The method of claim 1, wherein said tissue of the human body is selected from: the mouth, the lips or the teeth.

22. The method of claim 1 wherein said tissue of the human body is selected from: the epidermis, the epithelium of the oral cavity, the gastrointestinal tract or the female reproductive tract.

* * * * *